US009198576B1

(12) United States Patent
Barnes et al.

(10) Patent No.: US 9,198,576 B1
(45) Date of Patent: Dec. 1, 2015

(54) METHOD AND SYSTEM FOR MAKING OPHTHALMIC MEASUREMENTS

(71) Applicants: Ron Barnes, Dripping Springs, TX (US); Thomas Gosling, Lone Tree, CO (US)

(72) Inventors: Ron Barnes, Dripping Springs, TX (US); Thomas Gosling, Lone Tree, CO (US)

(73) Assignee: Hoya Corporation, Tokyo (JP)

(*) Notice: Subject to any disclaimer, the term of this patent is extended or adjusted under 35 U.S.C. 154(b) by 110 days.

(21) Appl. No.: 13/788,337

(22) Filed: Mar. 7, 2013

(51) Int. Cl.
*A61B 3/14* (2006.01)

(52) U.S. Cl.
CPC .......................................... *A61B 3/14* (2013.01)

(58) Field of Classification Search
CPC .......... A61B 3/14; A61B 3/111; A61B 3/152; A61B 8/10; G02C 13/003; G02C 13/005
USPC ............... 351/204, 206, 208, 159.75, 159.76, 351/178; 396/18, 52, 55
See application file for complete search history.

(56) References Cited

U.S. PATENT DOCUMENTS

| | | | |
|---|---|---|---|
| 4,845,641 | A | 7/1989 | Ninomiya et al. |
| 6,583,792 | B1 | 6/2003 | Agnew |
| 6,847,383 | B2 | 1/2005 | Agnew |
| 7,384,144 | B2 | 6/2008 | Ross-Messemer et al. |
| 8,355,862 | B2 | 1/2013 | Matas et al. |
| 2011/0298829 | A1* | 12/2011 | Stafford et al. ............... 345/659 |
| 2013/0278895 | A1* | 10/2013 | Pham et al. .................... 351/204 |
| 2014/0240470 | A1* | 8/2014 | Dias Da Silva et al. ........ 348/49 |

OTHER PUBLICATIONS

ABS ACEP Smart Mirror Mobile, published on Dec. 2, 2012 for download from the website http://download.cnet.com/Smart-Mirror-Mobile/3000-2064_4-12857948.html . Four pages.*
Zeiss, i.Terminal 2 by Zeiss product sheet, pp. 1-2, listed date 2011.
Optikam Tech Inc., Optikam Frame Selector Kiosk User Manual, pp. 1-28, no listed date, accessed Jan. 10, 2013.
Essilor, Visiooffice product sheet, pp. 1-10, listed date Mar. 2011.
Ollendorf, visuReal The Hardware product information, p. 1, listed date Jan. 2011.

(Continued)

*Primary Examiner* — Scott J Sugarman
*Assistant Examiner* — Gary O'Neill
(74) *Attorney, Agent, or Firm* — Grady K. Bergen; Griggs Bergen LLP

(57) ABSTRACT

A method of taking an ophthalmic measurement is carried out with an electronic handheld device having a touchscreen display and a camera unit for producing digital photographic images with the handheld device that are displayed on the touchscreen display in real time. The handheld device has a orientation sensing unit for determining the orientation of the handheld device. A subject is positioned wearing a spectacle frame on the subject's head at a position so that real time images of the subject's head with the spectacle frame from the camera unit are displayed in the touchscreen display. The electronic handheld device is moved with the real time images of the subject's head and eyewear being displayed within the display until the orientation sensing unit of the handheld device measures that the handheld device is at a selected oriented position. An image of the subject's head and eyewear are automatically captured and stored on the electronic handheld device at the moment the orientating sensing unit measures that the handheld device is at the selected oriented position. At least one ophthalmic measurement is made using the captured image.

20 Claims, 29 Drawing Sheets

(56) References Cited

OTHER PUBLICATIONS

Ollendorf, visuReal Inclination Sensor product information, p. 1, listed date Jan. 2011.

Ollendorf, visuReal new Premium product information, p. 1, listed date Jan. 2011.

Ollendorf, visuReal The Software product information, pp. 1-2, listed date Jan. 2011.

Ollendorf, visuReal All-in-One Measurement Tool product information, p. 1, listed date Jan. 2011.

Ollendorf, visuReal newPremium standAlone product information, p. 1, listed date Aug. 2011.

Ollendorf, visuReal newPremium full HD product information, p. 1, listed date Jan. 2012.

Ollendorf, visuReal portable product information, p. 1, listed date Jan. 2012.

Ollendorf, visuReal newPremium wireless product information, p. 1, listed date Jan. 2012.

Hoya Corporation, Description of Early iPhone Device, pp. 1-2, admitted prior art.

* cited by examiner

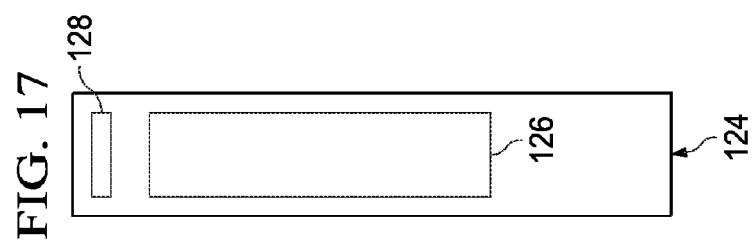
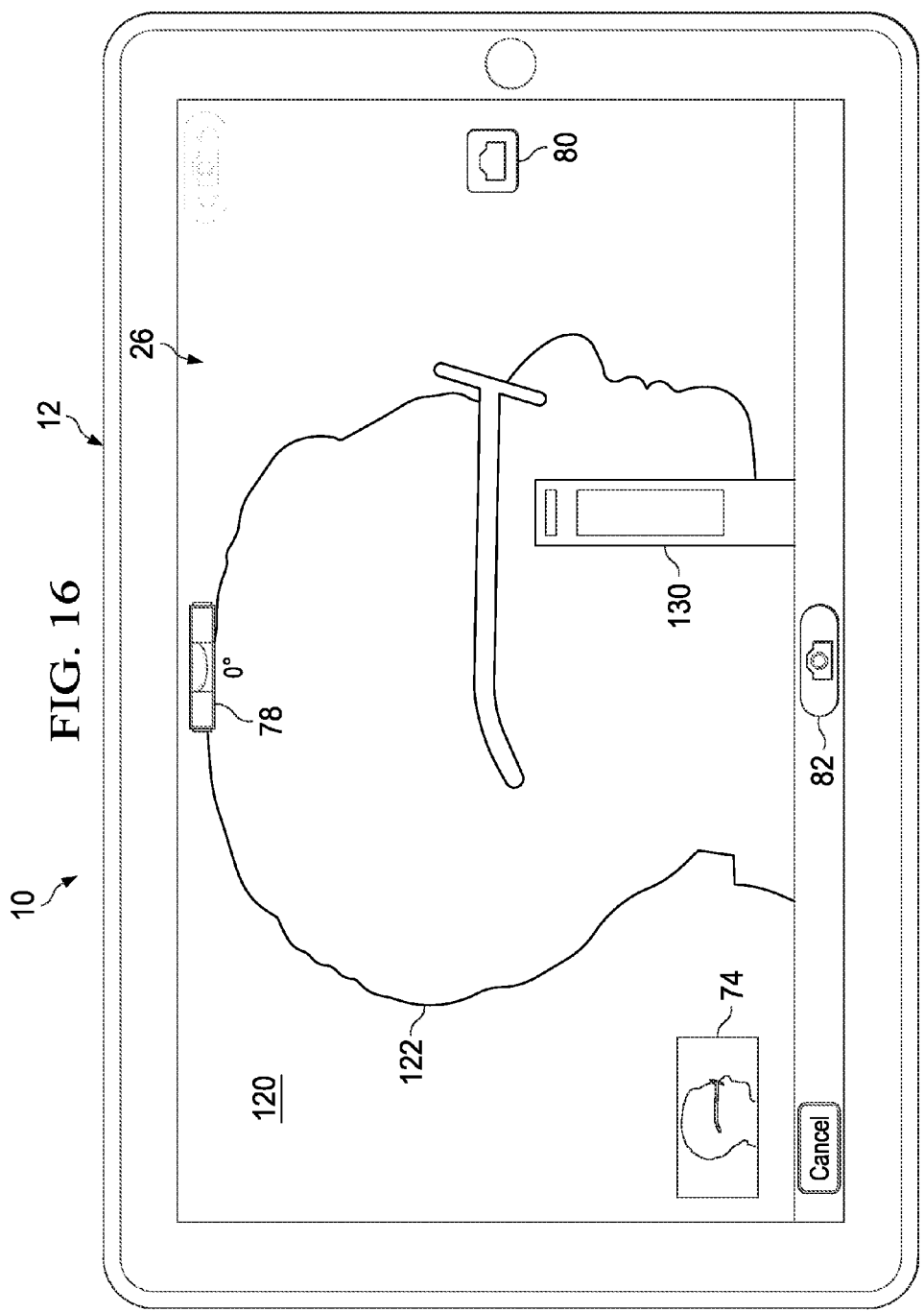

METHOD AND SYSTEM FOR MAKING OPHTHALMIC MEASUREMENTS

COPYRIGHT PROTECTION

A portion of the disclosure of this patent document contains material that is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

In the process of manufacturing corrective lenses for eyeglasses or spectacles used to correct defects in a person's vision, various factors may be used to form the final lenses. Integration of the lens into the selected frame and how the frame sits or rests on a person's face in relation to the person's eye(s) may need to be taken into account. Accordingly, various measurements may need to be taken to ensure that the lenses, once manufactured and mounted to the spectacle frames, are positioned so that the corrective properties of the lenses are optimized.

In the past, various measuring systems have been used to facilitate these measurements. The equipment, however, has tended to be large, complicated, and bulky, taking up valuable workspace. Because of its size, the equipment utilized in such measuring systems are usually stationary, requiring that the patient and optician or eye care professional move to the location where the measuring system is located, which may be inconvenient or out of the way. These systems also tend to be quite expensive, requiring a rather large capital investment by the optician or eye care professional.

Accordingly, a need exists for measuring systems that overcome these shortcomings.

SUMMARY

A method of taking an ophthalmic measurement for the customization of eyeglasses utilizes an electronic handheld device having a touchscreen display and a camera unit for producing digital photographic images with the handheld device that are displayed on the touchscreen display in real time. The handheld device has an orientation sensing unit for determining the orientation of the handheld device.

In carrying out the method with the handheld device, in an ophthalmic measurement selection mode of the device an ophthalmic measurement selection prompt is provided on the touchscreen display that allows the alternate selection of at least two different ophthalmic measurements for the customization of eyeglasses. In an image capturing mode of the device an ophthalmic measurement camera viewfinder screen is provided on the touchscreen display corresponding to the selected ophthalmic measurement made from the ophthalmic measurement selection prompt. A subject wearing a spectacle frame on the subject's head at a position is positioned so that real time images of the subject's head with the spectacle frame from the camera unit are displayed in the ophthalmic measurement camera viewfinder screen of the touchscreen display while in the image capturing mode. The electronic handheld device is moved with the real time images of the at least a portion of the subject's head and spectacle frame being displayed within the display until the orientation sensing unit of the handheld device measures that the handheld device is at a selected oriented position. Upon initiating an image capture instruction, a single, non-transitory digital photographic image of the subject's head and spectacle frame for the selected ophthalmic measurement is automatically captured and stored on the electronic handheld device only at the moment the orientating sensing unit measures that the handheld device is at the selected oriented position.

The method further entails, in an ophthalmic measurement mode of the device, providing an ophthalmic measurement screen on the touchscreen display. At least one ophthalmic measurement is made with the handheld device using the previously captured and stored single, non-transitory digital photographic image using an ophthalmic measurement device that is displayed on the touchscreen display that is manually manipulated to facilitate making the ophthalmic measurement. The ophthalmic measurement may be one of a pantoscopic tilt measurement, a face form angle measurement, a vertex distance measurement, a seg height measurement, a spectacle frame dimension measurement, and a pupillary distance measurement.

In another aspect of the invention, a mobile handheld ophthalmic measuring system is provided. The system includes a housing, a computer processing system, a touchscreen display, a camera unit for producing digital photographic images with the handheld device that are displayed on the touchscreen display in real time. The system further includes an orientation sensing unit for determining the orientation of the handheld device. A camera control allows the camera unit to be selectively switched to an image capturing mode, wherein the camera unit automatically captures an image at the moment the orientation sensing unit measures the handheld device is at a selected orientation. At least one ophthalmic measuring device that is usable with the captured image to make at least one ophthalmic measurement is also provided with the system.

BRIEF DESCRIPTION OF THE DRAWINGS

For a more complete understanding of the present invention, and the advantages thereof, reference is now made to the following descriptions taken in conjunction with the accompanying figures, in which:

FIG. 16 is a plan view of vertex distance viewfinder screen of the display of the device of FIG. 4 shown with a vertex distance ghost image in accordance with an illustrative embodiment of the invention;

FIG. 17 is a plan view of a lock-on device constructed in accordance with an illustrative embodiment of the invention;

FIG. 30 is a plan view of a patient information screen of the display of the device of FIG. 4 shown with patient information fields in accordance with an illustrative embodiment of the invention;

FIG. 31 is a plan view of the patient information screen of FIG. 30 shown with a virtual keyboard in accordance with an illustrative embodiment of the invention.

DETAILED DESCRIPTION

Figure 1:
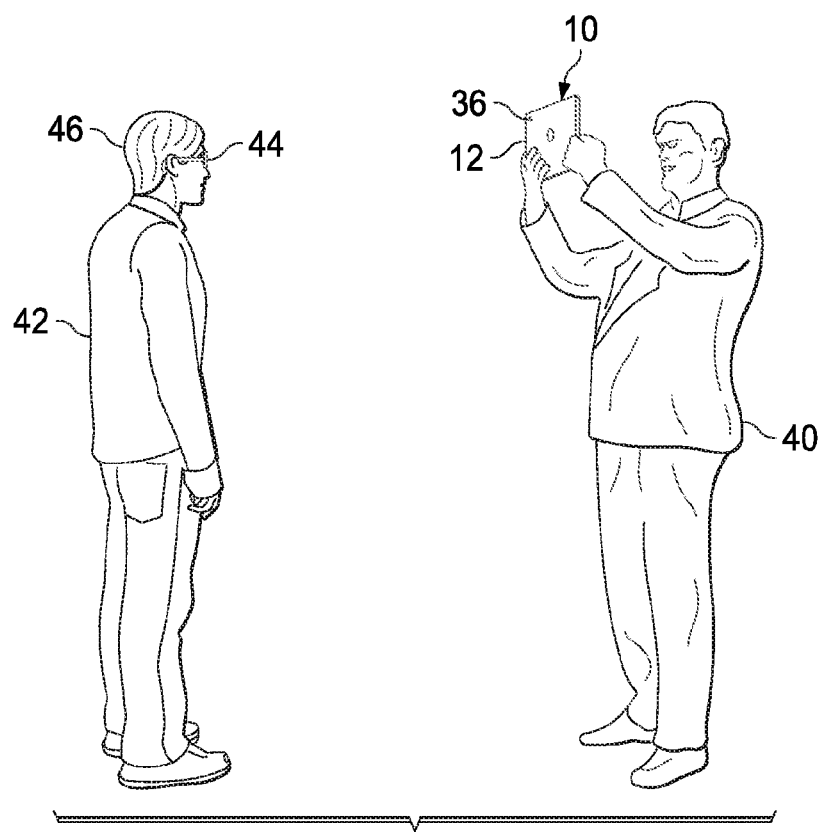
FIG. 1 is an illustration of an electronic handheld device being held and used by a user in making ophthalmic measurements for a subject wearing a set of spectacle frames.

Referring to FIG. 1, the invention utilizes an electronic handheld device 10. The handheld device 10 may include any electronic handheld computing device, such as a smart phone, tablet computer, or other device that is capable of functioning and being used in the manner described herein. In some cases, the device 10 may be a desktop device, such as a laptop, an all-in-one computer, etc., that is capable of being held and manipulated in a user's hands, but that may be normally be positioned on a desktop or other support surface except when performing certain operations. In other embodiments, the device 10 may be a handheld component of a system or device where portions of such system or device are not handheld and/or may be predominantly stationary during its use.

In many applications, however, the device 10 is an electronic mobile handheld device that is independent of other systems and is capable of fully performing the functions and operations as described herein, other than possibly a wireless communication link or a docking or charging station that may be used periodically. Such mobile handheld devices may include smart phones and tablet computers. In many instances, the mobile handheld device 10 will be a tablet computer, such as the IPAD® handheld computing device currently available on the market as of the date of this application.

In many embodiments, the mobile handheld device 10 is sized and configured so that it may be held and manipulated in one's hand or hands with little effort. The device 10 may have an overall width of from 4.0, 4.5, 5.0, 5.5, 6.0, or 6.5 inches to 7.0, 7.5, 8.0, 8.5, 9.0, 9.5, or 10.0 inches and an overall length of from 6.0, 6.5, 7.0, 7.5, 8.0, 8.5, 9.0, or 9.5 inches to 10.0, 10.5, 11.0, 11.5, or 12.0 inches. The thickness of the device 10 may range from 2.0, 1.0, 1.0, 0.5, or less. In many cases, the handheld mobile device will have a thickness 0.5, 0.4, 0.3 inch or less. The mobile device 10 will also be relatively light in weight, such as from 2.0 lbs, 1.5 lbs, 1.0 lb, 0.5 lb or less, so that it can be easily lifted, moved, or otherwise manipulated.

It should be understood that with respect to any amount or range listed or described in any summary or detailed description as being useful, suitable, or the like, it is intended to include every amount or point within the range, including the end points, and is to be considered as having been specifically stated. For example, "a range of from 1 to 10" is to be read as indicating each and every possible number along the continuum between about 1 and about 10. Thus, even if specific data points within the range, or even no data points within the range, are explicitly identified or refer to only a specific few, it is to be understood that the inventors appreciate and understand that any and all data points within the range are to be considered to have been specified, and that the inventors are in possession of the entire range and all points within the range, unless explicitly stated otherwise.

Figure 2:
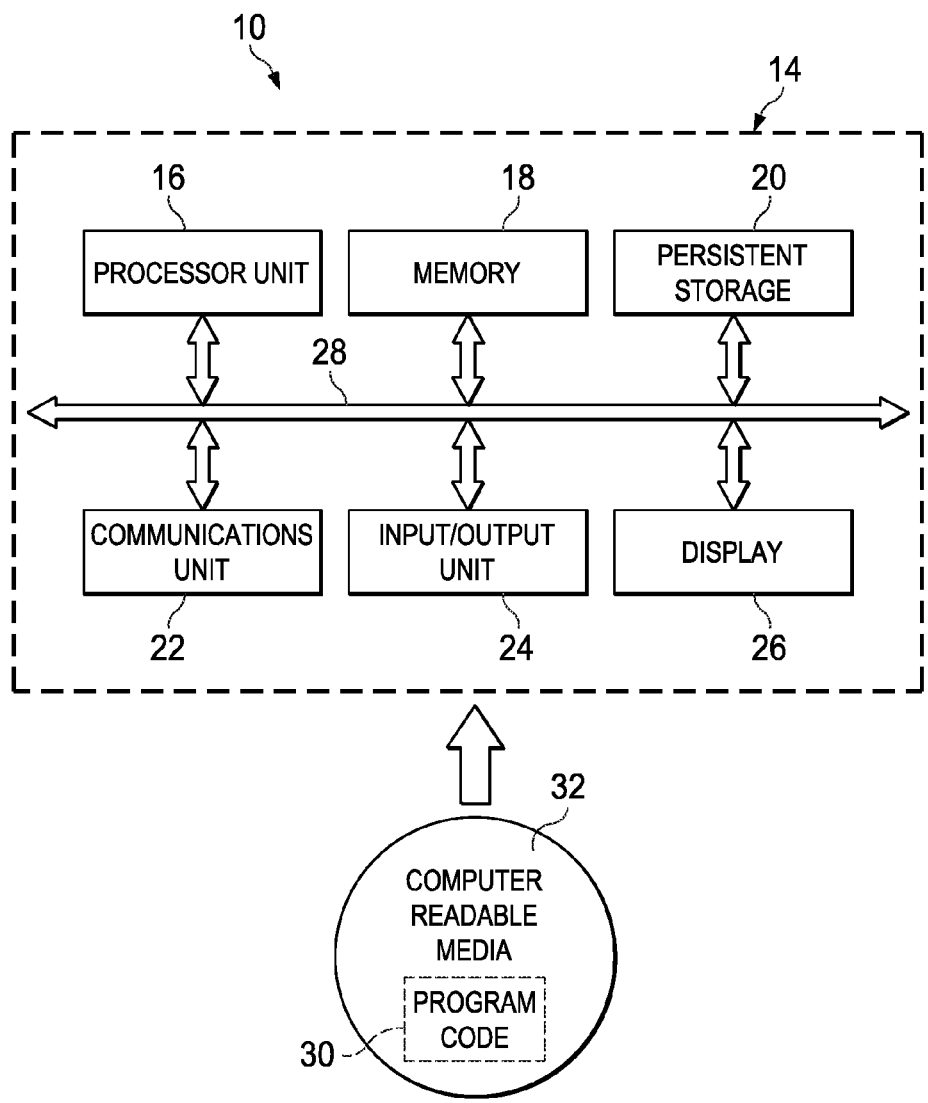
FIG. 2 is a schematic block diagram of a data processing system of the handheld device of FIG. 1 in which the illustrative embodiments may be implemented.

The handheld device 10 includes a case or housing 12 that houses the various components of the device. Referring to FIG. 2, a schematic block diagram of the some of the various components of the handheld device 10 is shown. The device 10 includes an overall data processing system 14 that includes a data processor unit 16, a memory unit 18, a persistent storage unit 20, a communications unit 22, an input/output (I/O) unit 24, and a display 26. The data processing system 14 further includes communications fabric 28, which provides communications between processor unit 16, memory 18, persistent storage 20, communications unit 22, input/output (I/O) unit 24, and display 26.

Processor unit 16 serves to execute instructions for software or programs that may be loaded into memory 18. Processor unit 16 may be a set of one or more processors or may be a multi-processor core, depending on the particular implementation. Further, processor unit 16 may be implemented using one or more heterogeneous processor systems in which a main processor is present with secondary processors on a single chip. As another illustrative example, processor unit 16 may be a symmetric multi-processor system containing multiple processors of the same type.

Memory 18 and persistent storage 20 are examples of storage devices. A storage device is any piece of hardware that is capable of storing information either on a temporary basis and/or a permanent basis. Memory 18, in these examples, may be, for example, a random access memory or any other suitable volatile or non-volatile storage device. Persistent storage 20 may take various forms depending on the particular implementation. For example, persistent storage 20 may contain one or more components or devices. For example, persistent storage 20 may be a hard drive or flash memory, a rewritable optical disk, a rewritable magnetic tape, or some combination of the above. The media used by persistent storage 20 also may be non-removable or removable. For example, a removable hard drive or flash memory may be used for persistent storage 20.

Communications unit 22, in these examples, provides for communications with other data processing systems or devices. In these examples, communications unit 18 is a network interface card or system. Communications unit 24 may provide communications through the use of either or both physical and wireless communications links.

Input/output unit 24 allows for input and output of data to and from the data processing system 16. For example, input/output unit 24 may provide a connection for user input through a keyboard, keypad, mouse, or touchpad. The input/output unit 24 may also constitute a touchscreen provided on the system 14 that is integrated with the display 26 and which may include a virtual keyboard and/or keypad. Further, input/output unit 24 may send output to the display 26 or other unit or device.

The display 26 provides a mechanism to display information to a user. This is typically in the form of an electronic digital display provided on a screen, such as an LCD, OLED or other display screen technology. In certain embodiments, the display 26 also serves as an interface for the input/output unit 24, such as through a touchscreen display, as previously discussed. In many embodiments, the input/output unit 24 will constitute a touchscreen that is formed from all or a portion of the display 26. The display/touchscreen 26 may form a majority of a surface of the mobile device 10. In certain cases, the display 26 may constitute from greater than 50%, 60%, 70%, 80%, 90% or more of a surface of the device 10. Such touchscreen displays of the device 10 may include resistive, capacitive, surface acoustic wave, or other touchscreens that may utilize pressure, conductive contact, or other means to manipulate the touchscreen. Manipulation of such touchscreens to provide data input or other means may be conducted with a user's finger(s) or with a suitable stylus or other device. The touchscreen display 26 may also be a multi-touch display that can sense multiple contact points. Other technologies for providing such touchscreen-like capabilities wherein input can be provided in combination with or through the display 26 may also be used. These may include those with non-contact touchscreen capabilities, such as those using optical or photosensors where actual physical contact with the touchscreen display is not required.

Instructions for the operating system and applications or programs are located on persistent storage 20. These instructions may be loaded into memory 18 for execution by processor unit 16. The processes of the different embodiments may be performed by processor unit 16 using computer implemented instructions, which may be located in a memory, such as memory 18. These instructions are referred to as program code, computer usable program code, or computer readable program code that may be read and executed by a processor in processor unit 16. The program code in the different embodiments may be embodied on different physical or tangible computer readable media, such as memory 18 or persistent storage 20.

Program code 30 may be located in a functional form on computer readable media 32 that is selectively removable and/or may be loaded onto or transferred to the mobile device for execution by processor unit 16. Program code 30 and computer readable media 32 form a computer program product in these examples. In one example, computer readable media 32 may be in a tangible form, such as, for example, an optical or magnetic disc that is inserted or placed into a drive or other device that is part of persistent storage 20 for transfer onto a storage device, such as a hard drive that is part of persistent storage 20. In a tangible form, computer readable media 20 also may take the form of a persistent storage, such as a hard drive, a thumb drive, or flash memory unit that is connected to device 10. The tangible form of computer readable media 32 is also referred to as computer recordable storage media. The computer recordable media 32 may be removable or non-removable from the device 10.

Alternatively, program code 30 may be transferred to the data processing system 14 from computer readable media 32 through a communications link to communications unit 22 and/or through a connection to input/output unit 24. The communications link and/or the connection may be physical or wireless in the illustrative examples. The computer readable media also may take the form of non-tangible media, such as communications links or wireless transmissions containing the program code.

In some illustrative embodiments, program code 30 may be downloaded over a network to persistent storage 20 from another device or data processing system for use with the device 10. For instance, program code stored in a computer readable storage medium in a server data processing system may be downloaded over a network from the server to the device 10, such as through the Internet. The data processing system providing program code 30 may be a server computer, a client computer, or some other device capable of storing and transmitting program code 30.

In the present invention, the program code 30 includes an ophthalmic measurement application or software. This application may be selected from other applications or programs that may be related or non-related to the ophthalmic measurement application. The features, operation and function of the ophthalmic measurement application are described in further detail later on. The ophthalmic measurement application may also include an eyeglass or spectacle ordering application or feature that allows the user to order eyeglasses or spectacles and/or lenses for such items using the device 10 based on the measurements made with the system. In certain embodiments, the ophthalmic measurement application is that which facilitates those measurements that may be necessary or useful to facilitate the manufacturing of free form lenses.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally may be referred to herein as a "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's system, partly on the user's system, as a stand-alone software package, partly on the user's system and partly on a remote system or entirely on the remote system or server. In the latter scenario, the remote system may be connected to the user's system through any type of network, including a local area network (LAN) or a wide area network (WAN), or the connection may be made to an external computer (for example, through the Internet using an Internet Service Provider).

Figure 3:
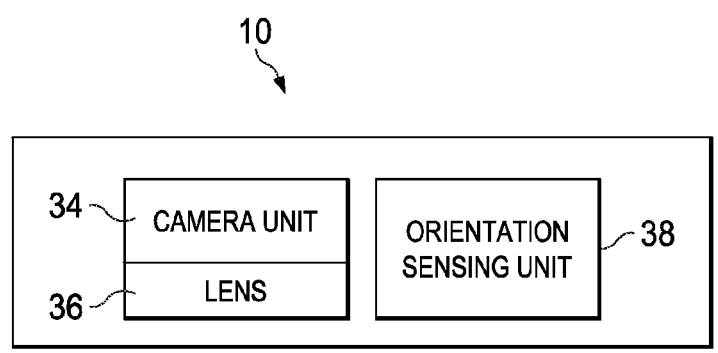
FIG. 3 is a schematic block diagram of a camera unit and orientation sensing unit of the device of FIG. 1 in which the illustrative embodiments may be implemented.

Referring to FIG. 3, a further block diagram of the mobile device 10 is shown. In particular, mobile device 10 is shown with a digital camera unit 34. The camera unit 34 is coupled to or otherwise in communication with the data processing system 14 (FIG. 2) to provide camera or image data to the data processing system 14. Alternatively, the camera unit 34 may have its own data processing system that is integrated or communicates with the data processing system 14. The camera unit 34 is that capable of producing and transmitting digital photographic images from a camera lens 36 of the camera unit 34 that is provided on the device 10 so that that the images are displayed continuously or substantially continuously on the display 26 in real time so that the images displayed on the display 26 generally correspond to what is being viewed through the camera lens 36. The display 26 thus constitutes a viewfinder of the camera unit 34, such as those viewfinders typically found on digital cameras as of the date of the present application. Appropriate software or computer programs for such camera unit 34 may be provided to the processing system 14 of the device 10 to provide such functionality. Other hardware necessary for the functioning and operation of the digital camera unit 34 may also be provided for the device 10.

An orientation sensing unit 38 is also provided with the device 10 and is coupled to the processing system 14. The orientation sensing unit 38 may include a digital accelerometer, a digital gyroscope, or a combination of both. Such electronic devices are typically microelectromechanical systems (MEMS). Such MEMS devices may be 1-, 2-, or 3-axes systems for measuring orientation with respect to 1, 2 or 3 axes of orientation, e.g., pitch, roll and yaw movement. In certain embodiments, a combination of accelerometer and gyroscopic sensors may be used to provide 6-axes or even 9-axes of orientation. The orientation sensing unit 38 may also provide a measurement of orientation about gravity. The orientation sensing unit 38 provides an indication or measurement of the orientation of the device 10. A non-limiting example of a commercial MEMS gyroscope is that manufactured by STMicroelectronics and marketed as L3G4200D.

The orientation sensing unit 38 is coupled to the processing system 14 and provides a data output with regard with the orientation of the device 10. This should include at least an indication of the orientation of the device 10 with respect to a single axis, which may be a vertical or horizontal axis. In some embodiments, the orientation sensing unit 38 provides an output or measurement with respect to the orientation of the device relative to a level position as measured about a single axis. In one aspect of the present invention, the orientation sensing unit 38 is coupled to the camera unit 34, such as by way of the processing system 14, that forms a camera control feature or function to facilitate capturing and storing of images with the camera unit 34 only when the orientation sensing unit 38 measures that the device 10 is at a selected orientation, as will be discussed in more detail later on.

The handheld device 10, as it has been described, in combination with the ophthalmic measurement application, which is provided as a computer program 30, forms the ophthalmic measurement system. As used herein, references to the device 10 may be made for convenience when describing the operation and use of the ophthalmic measurement system. It is to be understood that the device 10 includes the ophthalmic measurement application and thus constitutes the ophthalmic measurement system in conjunction with any other components described herein. The terms "device" and "system" with respect to the device 10 may therefore also be used interchangeable in the present description.

The ophthalmic measurement system 10 is used in a method of taking an ophthalmic measurement or measurements. Referring to FIG. 1, the person or user 40, which may be an optician or eye care professional, taking the measurement(s) using the device 10 is positioned adjacent or near a patient or individual subject 42 that is provided with a set of eyeglass or spectacle frames 44 that are worn on the subject's head 46 in the manner the spectacles 44 would normally be worn by the subject 42. An optician or other eyeglass professional may initially assist the subject in selecting a set of frames 44 that are appropriate for the individual. As used herein, the frames 44 are meant to include the spectacle frames with or without lenses attached. Such frames may be provided to the subject by the optician or eyeglass professional as demonstration frames for purposes of fitting and ophthalmic measuring purposes and thus may be provided with without lenses or with sample lenses. The frames 44 may also include rimless or partially rimless frames that do not have rims surrounding the lenses or portions of the lenses. In such rimless or partially rimless frames 44, sample lenses may be mounted to the bridge and temples of the frame 44. In such cases, ophthalmic measurements are made using the lenses themselves for the frame measurements. Thus, the lenses of the rimless or partially rimless frames also constitute part of the frame for measuring purposes.

Figure 4:
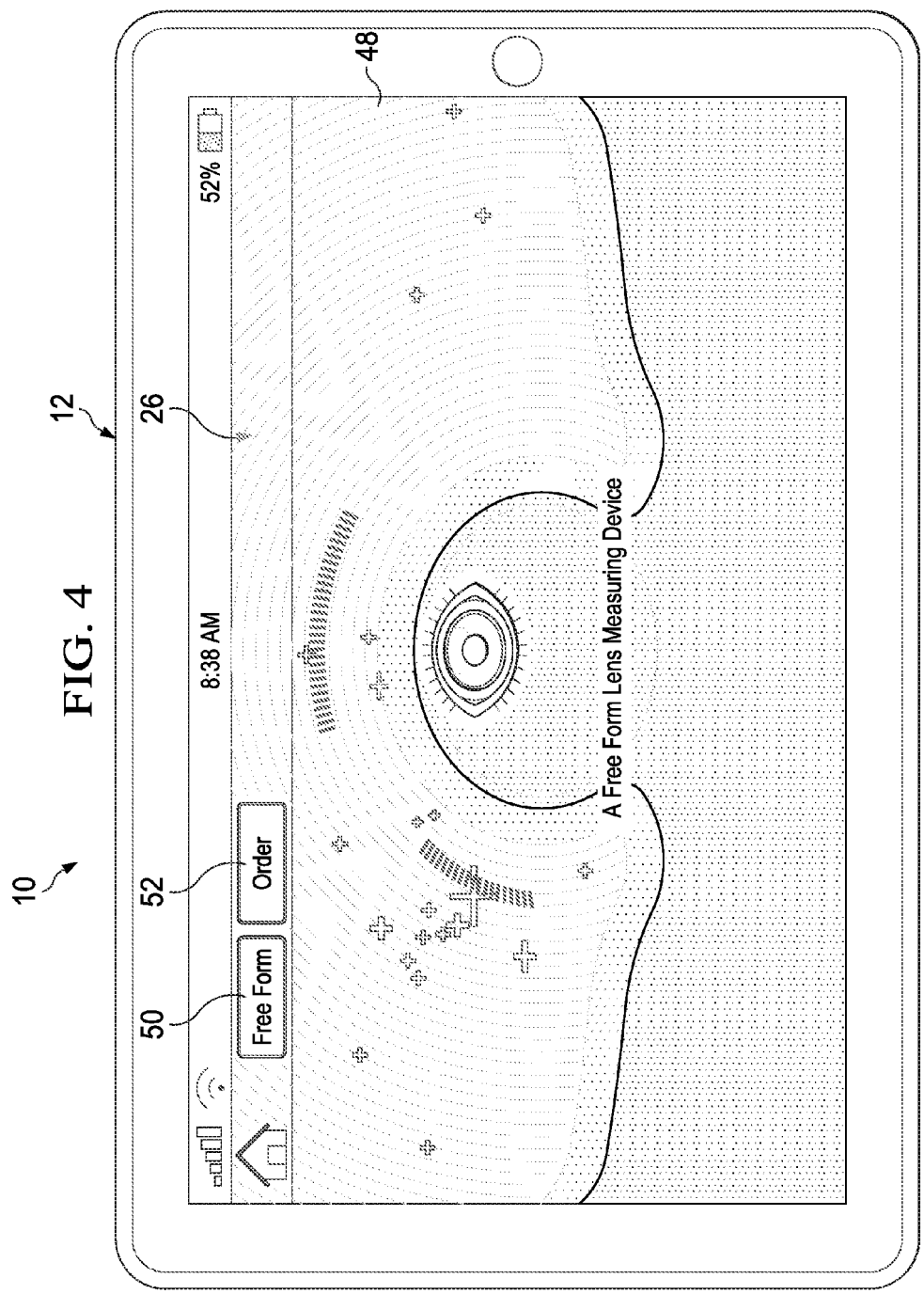
FIG. 4 is a plan view of an introductory screen of a display of the device of FIG. 1 in accordance with an illustrative embodiment of the invention.

The user 40 of the device 10 will launch the ophthalmic measurement application of the device 10. In the embodiment of FIG. 4, the device 10 is shown as an IPAD® handheld computing device, although other devices may be used. The device 10 may provide a welcome or introductory screen 48 on the display 26 of the device 10, as shown in FIG. 4. Each of the screens provided on the display 26, as discussed herein, may take up all or a portion of the display 26 of the device 10. In many instances, the screens may take up all or a majority of the display 26. In certain instances, a logon screen or field (not shown) may be provided with the introduction screen 48 that requires the user to login with a user name and/or password or otherwise prompts the user to create such information that permits the user to access the ophthalmic measurement application and/or associated data.

Selection icons or tabs 50, 52 may be provided that allow the user to select aspects of the ophthalmic measurement application. These icons, as well as other icons discussed herein, may constitute controls of the system 10 through the display 26, which may be in the form of a touchscreen, as previously discussed. Such icons therefore may be activated or manipulation with the finger(s), hand, stylus, etc. At least some of the icons themselves may therefore form part of the input of the input/output unit 24. In other embodiments, a cursor controlled with a mouse touchpad or other device may be used to activate or manipulate the icons alternatively to the touchscreen or where the display 26 does not constitute a touchscreen.

The selection icons may include a measurement icon 50 and a lens ordering icon 52, for ordering lenses after the ophthalmic measurements are complete. These icons may be viewable on all or some of the screens of the display 26 when the application is launched and running.

Figure 5:
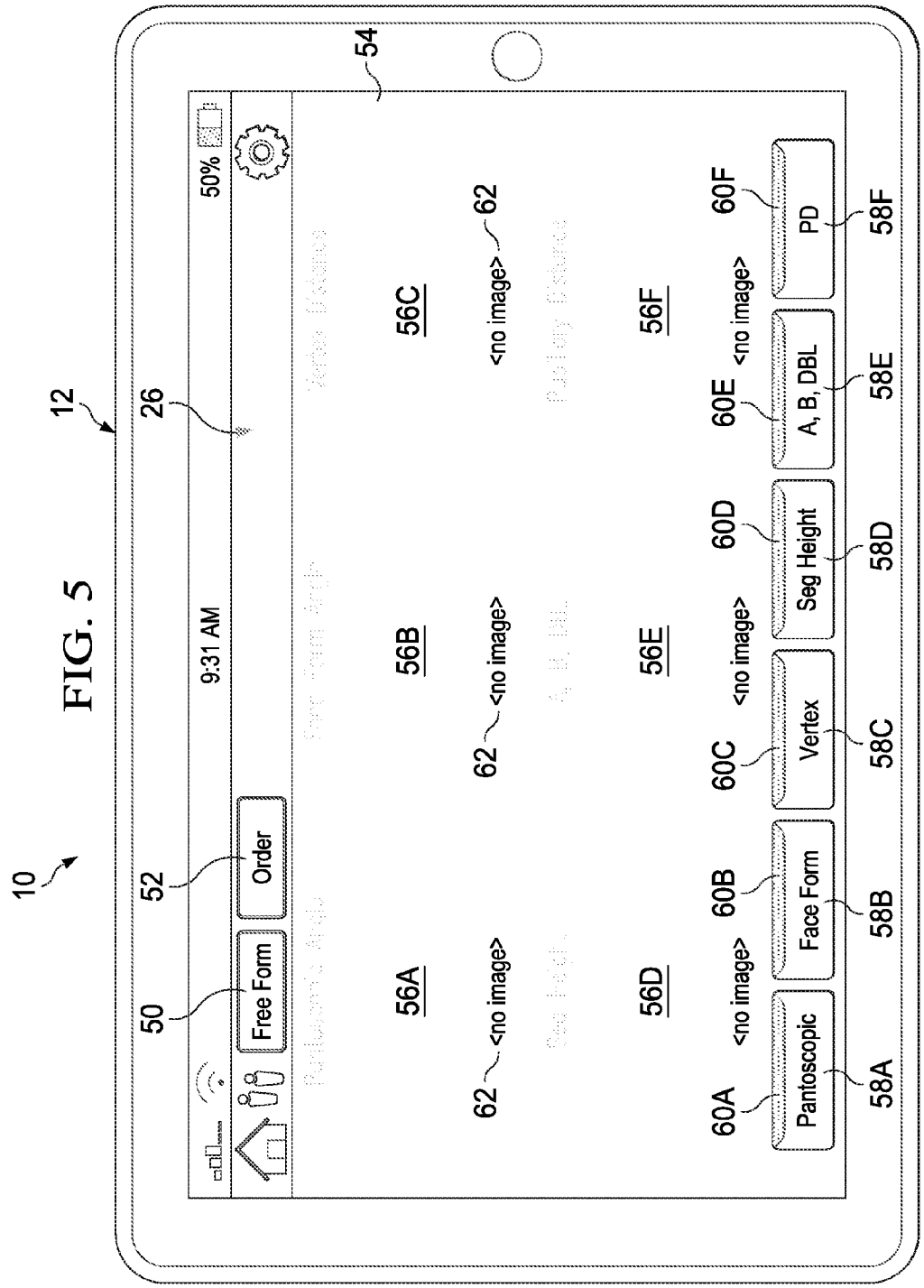
FIG. 5 is a plan view of a main measurement screen of the display of the device of FIG. 4 in accordance with an illustrative embodiment of the invention.

Upon selection of the measurement icon 50, a measurement main screen 54 is presented, as shown in FIG. 5. The main measurement screen 54 is divided into six (6) quadrants 56A-56F. Fewer or more quadrants may also be provided in some embodiments. The six quadrants correspond to six different ophthalmic measurements that may be taken using the system 10. These measurements may be those associated with or used in the manufacture of free form lenses. The quadrants of the main measurement screen 54 may be labeled or provided with indicia to indicate the particular measurement associated with each quadrant, as is shown. In the embodiment shown, quadrant 56A constitutes a pantoscopic angle or tilt measurement quadrant; quadrant 56B constitutes a face form angle measurement quadrant; quadrant 56C constitutes a vertex distance measurement quadrant; quadrant 56D constitutes a seg height measurement quadrant; quadrant 56E constitutes a spectacle frame dimension measurement (e.g., A, B, DBL dimensions) quadrant; and quadrant 56F constitutes a pupillary distance measurement quadrant. These may be provided in different orders or configurations to that shown.

Additionally, separate measurement icons or tabs 58A-58F may also be provided that correspond to the different quadrants 56A-56F, respectively. These may be located along a side edge of the display 26, such as a top, bottom, left or right side edge, or other area of the display 26. These icons 58A-58F are also provided with labels or indicia to indicate the particular measurement associated with each icon 58. In the embodiment shown, the icons 58 are also each provided with an appearance alter feature wherein the appearance of each icon 58 is changed depending upon a status with respect to each of the measurements. In the embodiment shown, the appearance alter feature constitutes a status bar or portion 60 of the icon 58. The status bar 60 is provided with an initial selected color or appearance to indicate a particular status. Upon operation or completion of a measurement corresponding to the particular icon 58, the appearance alter feature causes the icon 58 to change in appearance, such as a change in the color of the status bar 60. The appearance alter feature may also include a change in color, shading, the presentation or absence of a further icon or indicia on all or a portion of the icon 58 to indicate a particular status. In the embodiment shown, the status bars 60A-60F are initially displayed in the color red to indicate that no measurements have been completed for any of the measurements.

Additionally, the quadrants 56 of the main measurement screen 58 are blanked or provided with an indication 62, such as the label "no image," as shown, or other label to indicate that the measurement for that quadrant has not yet been completed.

To perform a specific measurement, the user may touch an area of one of the quadrants 56 or the measurement icon 58 corresponding to the selected measurement to be made. This launches a measurement screen for the corresponding measurement.

Figure 6:
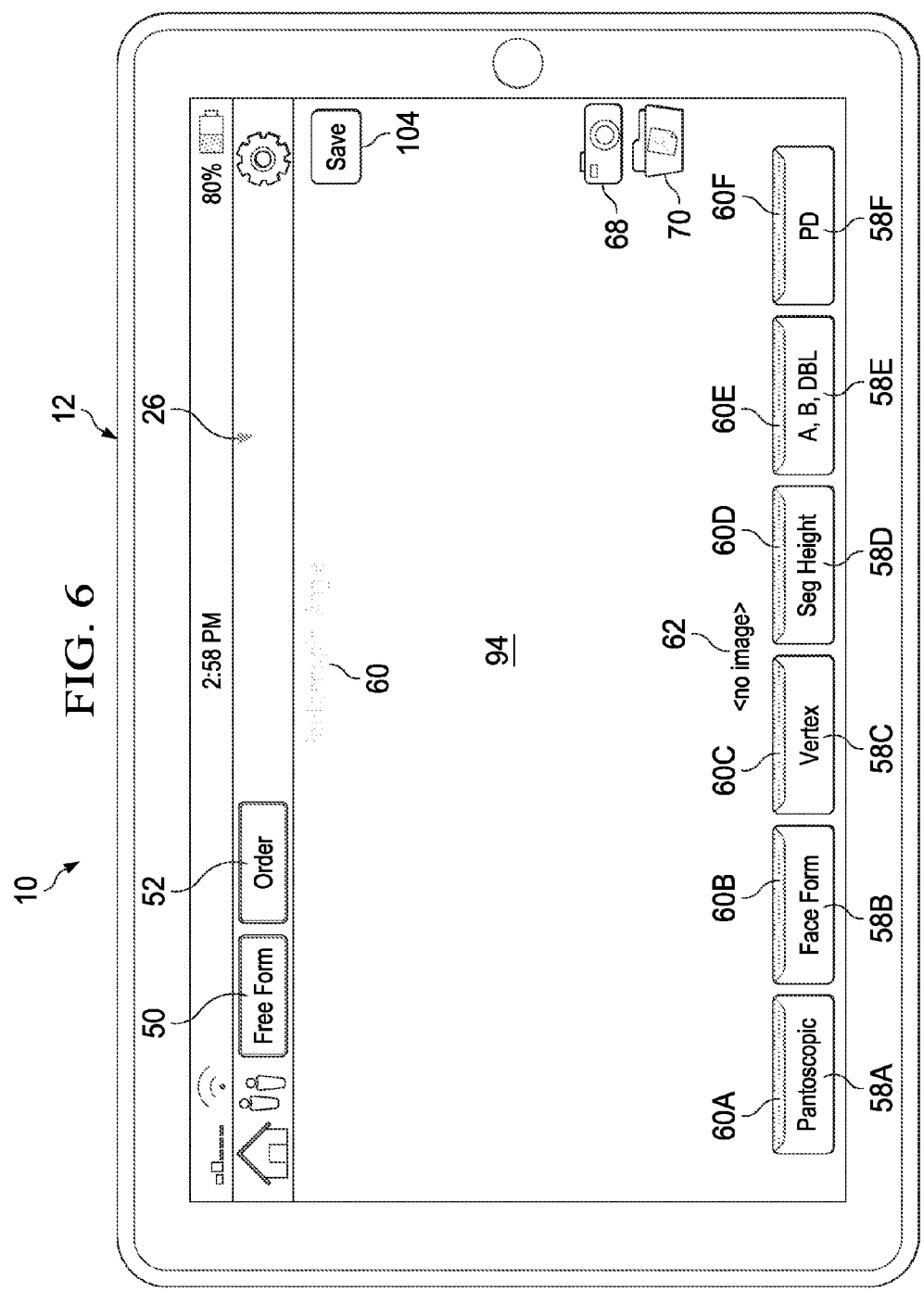
FIG. 6 is a plan view of a pantoscopic measurement screen of the display of the device of FIG. 4 presented without an image for measuring in accordance with an illustrative embodiment of the invention.

Thus, by activating the pantoscopic angle measurement icon 58A or quadrant 56A, a pantoscopic angle measurement screen 64 is opened in the display 26, as shown in FIG. 6. The pantoscopic angle measurement screen 64 as well as the other individual measurement screens may constitute an enlarged version of their respective measurement quadrants 56A-56F. As can be seen, the screen 64 is labeled with a measurement designation label 66 (e.g., "Pantoscopic Angle") to provide an indication of the measurement to be performed at the particular screen. An indication or label that no image is available or provided for the measurement may also be present on the screen 64. Such indication may also be provided on the other individual measurement screens where no image has been assigned for the particular measurement. Provided on each measurement screen, as with the measurement screen 64, are selection icons 68, 70. Icon 68 constitutes a camera icon and icon 70 constitutes a file icon. By activating file icon 70 the user is provided with an option to select a stored photo that has already been taken for the pantoscopic angle measurement using the system 10 or another system that is previously stored on the device 10 or is transmitted to the device 10 from a remote storage location where the image is stored.

Figure 7:
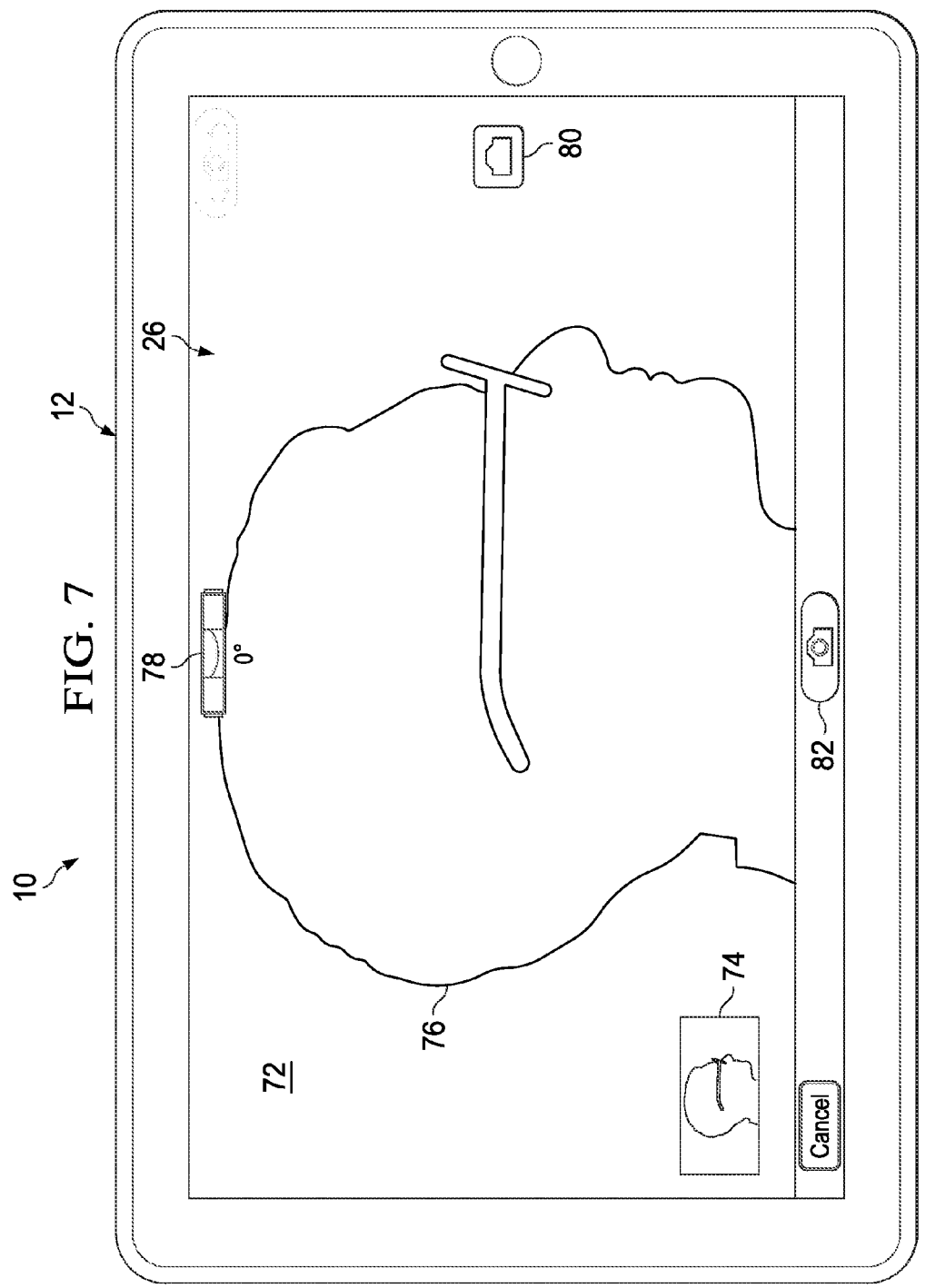
FIG. 7 is a plan view of a pantoscopic camera viewfinder screen of the display of the device of FIG. 4 shown with a pantoscopic ghost image in accordance with an illustrative embodiment of the invention.

By activating the camera icon 68, a pantoscopic camera viewfinder screen 72 is opened within the display 26, as shown in FIG. 7. A "ghost image" icon 74 is generated or provided in the screen 72 of the display 26. By activating the ghost image icon 74, a shadow or ghost image 76 is provided on the screen 72. The ghost image 76 may constitute a transparent or translucent image template that approximates the image of a side profile of a human's head and face, and may include an image of a pair of spectacle frames resting on the face, as is shown. The transparent or translucent property of the ghost image 76 allows the real time images of the subject to be transmitted through the ghost image 76. This prompts the user of the device 10 of the type of image to be taken with the device for pantoscopic measurements, i.e., that of the side profile of the subject. The ghost image 76 may also approximate the size and position of the head as it should appear in the viewfinder screen 72. By positioning the subject's head generally within the area of the ghost image 76 as it is viewed through the screen 72, the user is provided with an indication of the position the subject should be when the user is taking a photo of the subject with the device 10.

An orientation indicator 78 is also provided on the pantoscopic viewfinder screen 72. The orientation indicator 78 is provided with orientation information from the orientation sensing unit 38, previously discussed. The orientation indicator 78 may be in a variety of forms. In the embodiment shown, the orientation indicator 78 is in the form of a graphical representation of bubble level and a numerical value of angular displacement (e.g., degrees) about an axis. In the embodiment shown, the orientation indicator reflects the orientation or levelness of the device 10 with respect to a horizontal axis that passes through the device 10 to indicate when the device 10 is in a level or non-level position. In some embodiments, the orientation indicator 78 may be configured to provide orientation information with respect to angular position of the device 10 with respect to two or more axes. Thus, the orientation indicator may provide an indication regarding angular displacement about a horizontal axis and vertical axis.

Maintaining the device 10 in a level position when capturing the subject's photo for the various measurements is important because the orientation of the device 10 in a tilted, non-level position or improper orientation when images are captured may add error into the measurements, either adding to or subtracting from the values of the particular measurements made with the device.

A shutter-release icon 80 is provided on the pantoscopic viewfinder screen 72 to actuate the camera unit 34 for capturing and storing an image exposure. The shutter-release icon may be located along a side edge, such as the left or right side, of the screen so that it may be readily accessed with the user's thumb as they are holding the device 10. Other controls, such as the shutter-release icon 82, may also be provided on the device 10 for actuating the camera unit 34.

Figure 8:
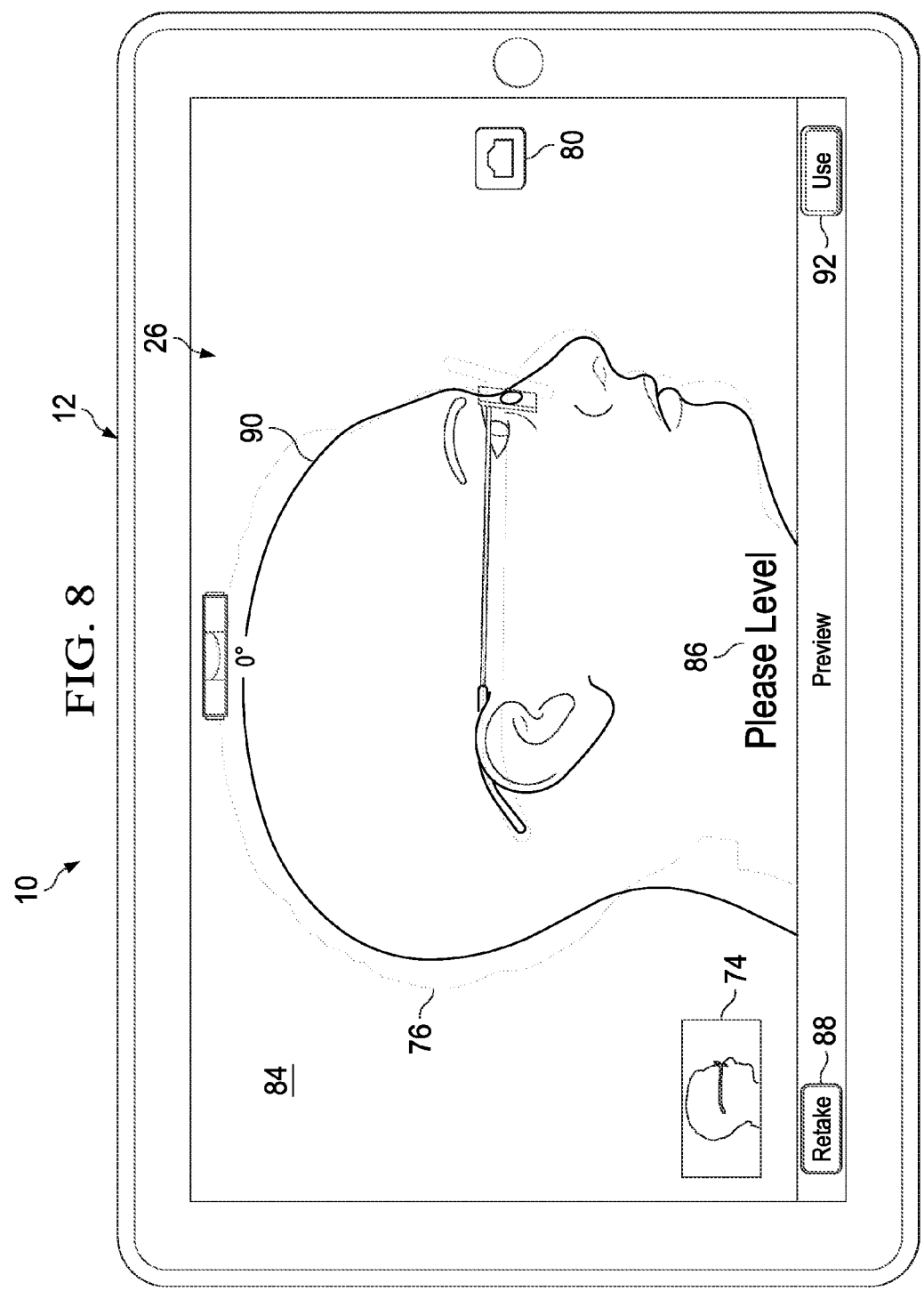
FIG. 8 is a plan view of the pantoscopic camera viewfinder screen of the display of the device of FIG. 7 shown with the image of a subject overlaying the pantoscopic ghost image in accordance with an illustrative embodiment of the invention.

Before the picture is taken, the subject may be instructed as to the proper position the subject should be in to perform the pantoscopic measurements. With respect to the pantoscopic angle, the subject may be instructed to look straight ahead while holding their head level. When the subject's profile is properly positioned within the viewfinder screen 72, as may be facilitated by the ghost image 76, the user may press or actuate the shutter-release icon 80. When the shutter-release icon 80 is actuated, a preview screen 84 (FIG. 8) with an orientation prompt indication 86 (e.g., the words "please level") may be provided in the viewfinder screen 72 to prompt the user to orient the device 10 to the proper orientation, e.g., a level position, for taking of the subject's image to be used for pantoscopic measurements. The orientation indicator 78 provides information to the user to facilitate orienting the device 10 to the proper orientation. The user will then rotate or move the device 10, while the subject remains positioned in the viewfinder screen 72, until a level or proper orientation is achieved.

After the shutter-release icon 80 or other shutter-release controls are actuated, as soon as the device 10 is in the selected orientation, as measured by the orientation sensing unit 38, the camera unit 34 will automatically capture and store the image within the viewfinder screen 72 at the moment the orientation sensing unit 38 measures that the device 10 is at the selected orientation, e.g., a level position. Program code or software that provides this function may be provided to the processing system 14 for this purpose. This captured and stored image constitutes the image that may be used for the pantoscopic measurements. No images may be captured with the device 10 until the orientation sensing unit 38 measures that the selected orientation of the device 10 has been achieved after the shutter-release icon 80 or controls are actuated to actuate the camera unit 34. Thus, activating the shutter-release icon 80 does not cause the camera unit 34 to capture and store the image until this selected orientation has achieved. In this way, the user is assured that the captured image for the pantoscopic measurements are made at the precise orientation. This removes any human error that may occur in orienting the device 10 to the selected orientation when the image is captured.

In some embodiments, an automatic capture override feature may be provided so that the user can disable the automatic capture and actuate the camera unit 34 manually or the automatic capture feature may be eliminated from the system 10 entirely. In such cases, the user may use or refer to the orientation indicator 78 while taking the photo and actuate the shutter-release icon 80 or 82, which immediately actuates the camera unit 34, without use of any automatic capture based on the measured orientation of the device.

Once the image is captured, if the user is not satisfied with the photo as shown in the preview screen 84, the user may retake the photo of the subject's image. A retake photo icon 88 may be provided for this purpose to restart the image capturing process and the process may be repeated, as previously described.

If the user is satisfied with the subject's image 90, the user saves and stores the image for use in pantoscopic measurements. A use-image icon 92 may be provided to instruct the system 10 to store the captured image 90 for use in making pantoscopic measurements.

Figure 9:
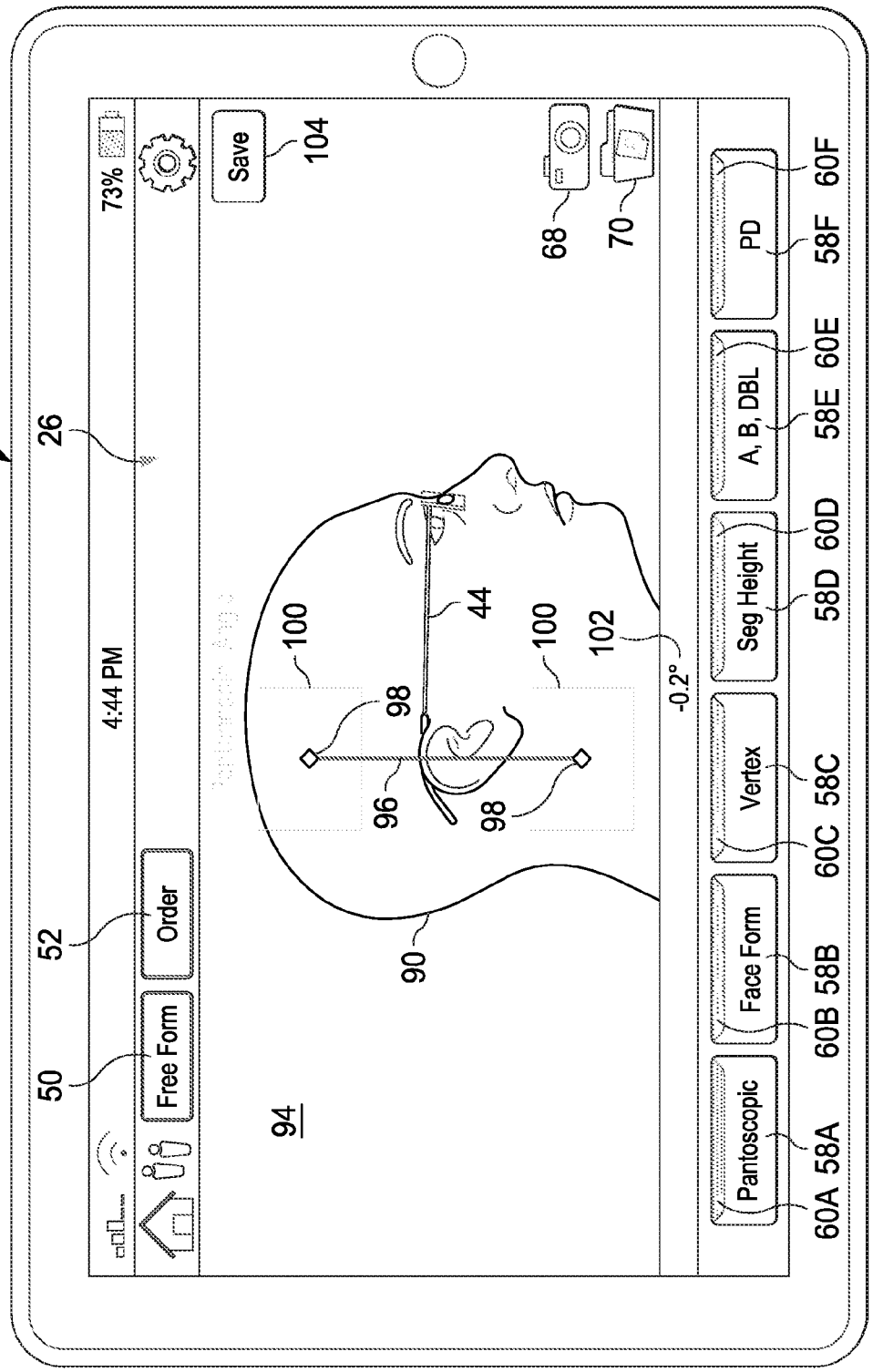
FIG. 9 is a plan view of the pantoscopic measurement screen of the display of the device of FIG. 4 shown with a captured image of the subject for use in performing pantoscopic measurements in accordance with an illustrative embodiment of the invention.

As shown in FIG. 9, upon storing of the image 90, the user may be taken to a pantoscopic angle or pantoscopic tilt measurement screen 94 where the image 90 is displayed. The status bar 60A may be changed to a different appearance or color, e.g., orange, to indicate that the pantoscopic angle measurement is in process but not yet complete. Additionally, a pantoscopic angle measurement device in the form of a straight line 96 having opposite endpoints or miers 98 is also generated and provided on the screen 94. The line 96 can be manipulated with the user's fingers or with a stylus to reposition or to change the length of the line through the touch-screen capabilities of the display 26. This may be accomplished by touching an active area 100 corresponding to and surrounding each of the miers 98. A demarcation may be provided around the active area 100 of the miers 98 to indicate the surrounding area that can be touched to move the line 96. When the active area 100 of one of the miers 98 is touched it may cause a change in appearance of all or a portion of the line 96, such as from red to green. This indicates that the line 96 or portion thereof is active and can be moved.

With the line 96 active, the line 96 may lengthened, shortened or be dragged or moved to different positions on the screen 94. To lengthen or shorten the line 96, the active area 100 of only a single mier 98 is touched by the user. The other mier 98 will remain stationary so that the line 96 can be lengthened, shortened or pivoted about the stationary mier. Movement of the entire line 96 across the screen 94 may be achieved by placing one's fingers on the active areas 100 of both miers 98 and sliding or dragging the line 96 into a desired position.

Figure 10:
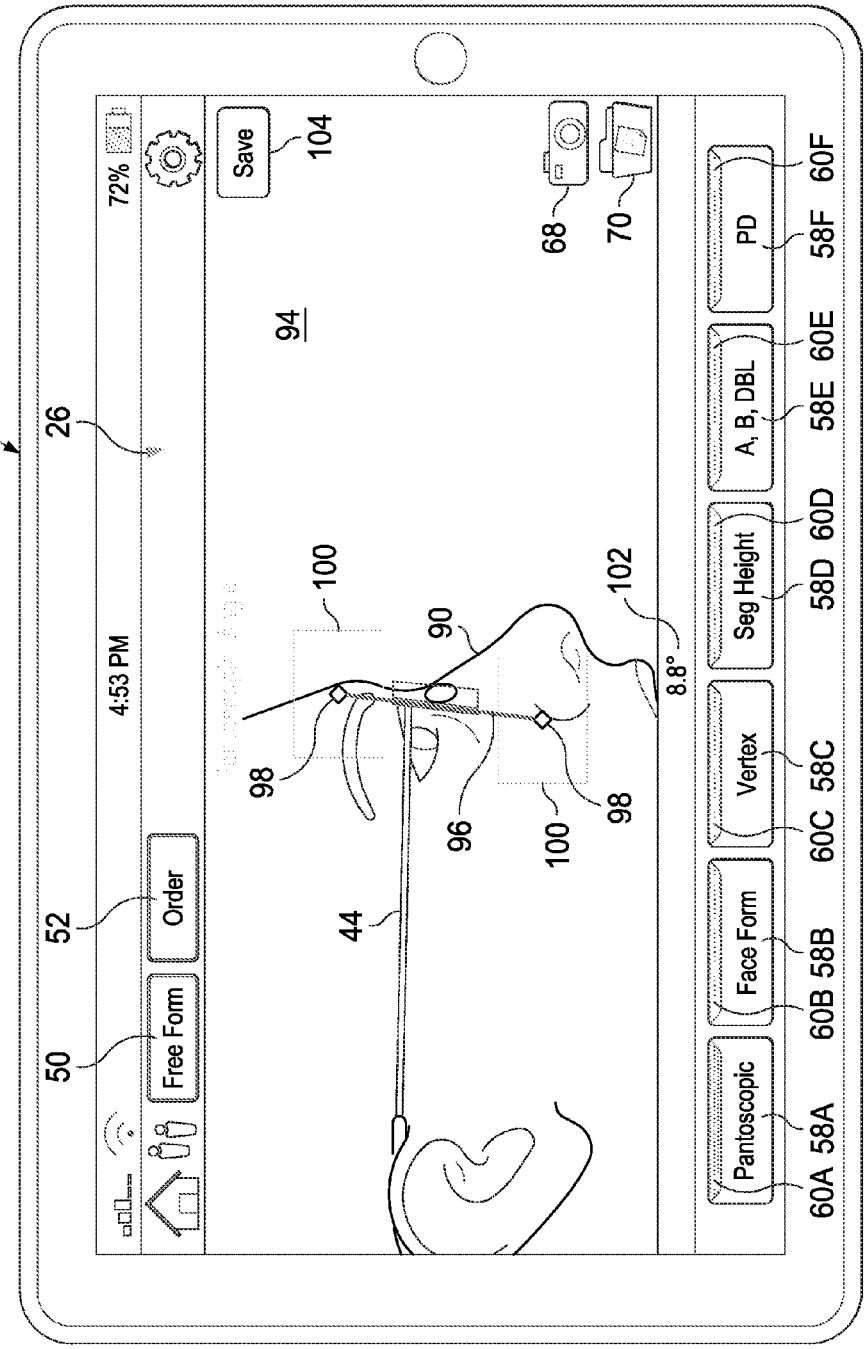
FIG. 10 is a plan view of the pantoscopic measurement screen of FIG. 9 shown with an enlarged area of captured image of the subject for use in performing pantoscopic measurements in accordance with an illustrative embodiment of the invention.

The image 90 can also be moved and enlarged for more precise measurements, if necessary, as shown in FIG. 10. Enlargement may be accomplished by using a multi-finger touch of the touchscreen wherein the multiple fingers are spread apart over the touchscreen to increase the size of the image 90 in the area surrounding the fingers. Likewise, the size of the image 90 may also be reduced by pinching or squeezing the fingers together over the touchscreen. Other means for enlargement or reduction in size of the image 90 may also be used, such as multiple tapping (e.g., double tapping) or prolonged contact for a selected period of time or increased pressure of the touchscreen in the area of the image 90 to be enlarged or reduced.

To perform a pantoscopic angle measurement, the line 96 is moved to a position over the front of the side edge of the eyeglass frame 44, as shown in FIG. 10, to determine the pantoscopic angle. An angle readout 102 may be displayed on the screen 94 to indicate the angle of the line 96. The pantoscopic angle or pantoscopic tilt is the angle of the plane or forward tilt of the spectacle lens (or frame) as viewed from the side of the lens (or frame) relative to a vertical line or axis, which represents the vertical plane of the subject's face. The pantoscopic angle is usually within the range of from 7° to 12°.

When the user is satisfied that the line 96 is properly positioned over the side edge of the frame 44, the user may activate a save icon 104, which saves the measurement. Saving may also include saving all or a portion of the information included on the pantoscopic screen 94 at the moment the save icon 104 is activated. This may include the captured image 90, as well the final position of the line 96 over the frame 44, and the value of the measured angle.

Figure 11:
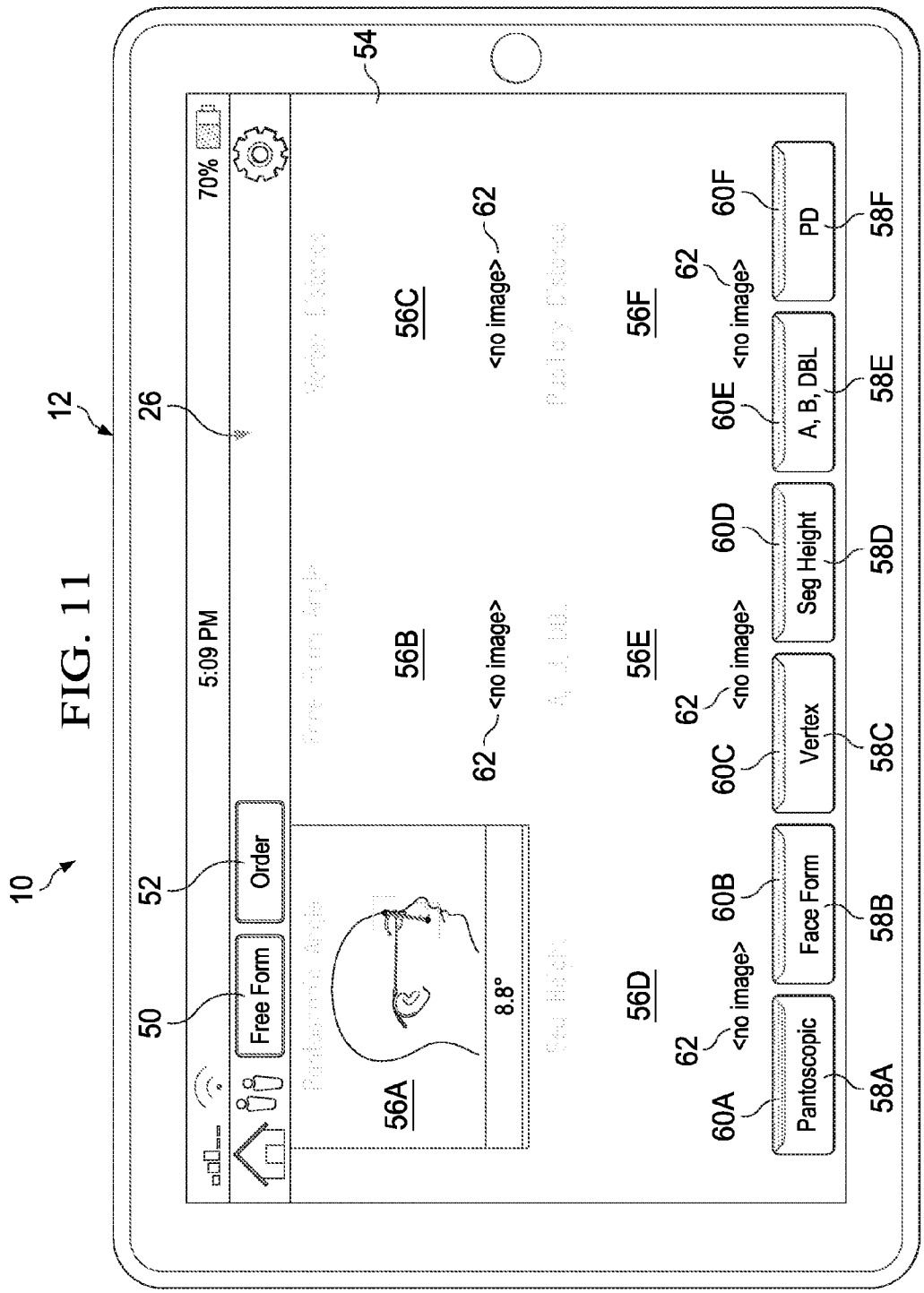
FIG. 11 is a plan view of the main measurement screen of the display of the device of FIG. 5 shown with a completed pantoscopic angle measurement quadrant in accordance with an illustrative embodiment of the invention.

Activating the save icon 104 may also close the pantoscopic screen 94 and automatically take the user to the main measurement screen 54 (FIG. 11). As shown in FIG. 11, the saved information from the pantoscopic angle screen 94 is now presented in quadrant 56A of the main measurement screen 54. In other embodiments, activating the save icon 104 may present the user with another screen, such as the screen for the next measurement to be performed. Additionally, the status bar 60A may also be changed in appearance upon the saving of the pantoscopic measurement. Here the status bar 60A is presented in the color green to indicate that the pantoscopic measurement is complete.

Figure 12:
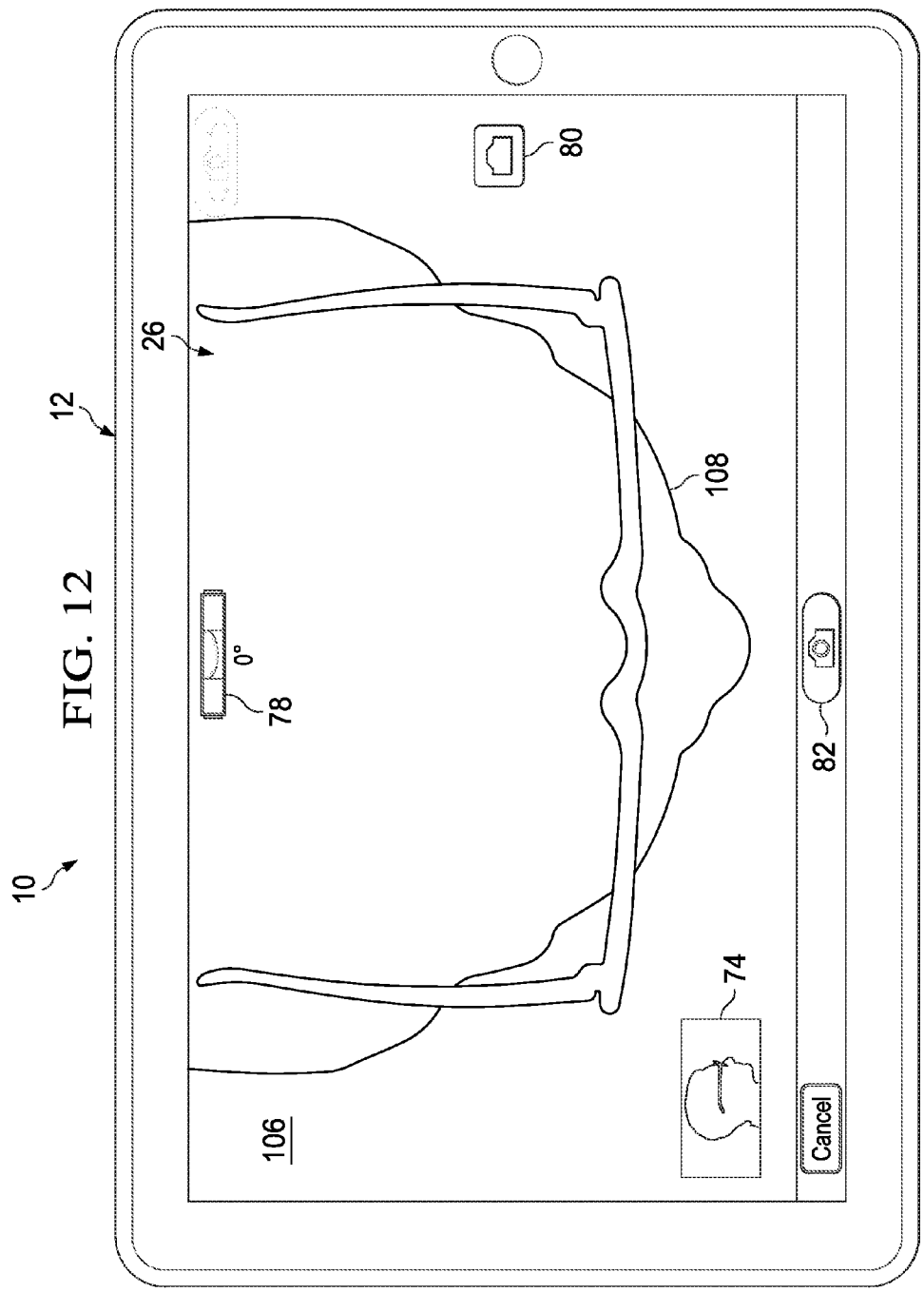
FIG. 12 is a plan view of face form viewfinder screen of the display of the device of FIG. 4 shown with a face form ghost image in accordance with an illustrative embodiment of the invention.

To take the next measurement, the user actuates one of the remaining quadrants 56B-56F or measurement icons 58B-58F. In the current example, the user may actuate quadrant 56B or measurement icon 58B, which is for measuring the face form angle. As with the pantoscopic measurement screen 64, this opens a face form measurement screen where the user selects the camera icon 68 or file icon 70 to take a photo or select a previously stored photo. An indication or label (not shown) that no image is available or provided for the face form angle may also be present on the face form measurement screen, as previously discussed. Upon selection of the camera icon 64 of the face form measurement screen, a camera viewfinder screen 106 is opened, as shown in FIG. 12. The face form camera viewfinder screen 106 may be similar to the pantoscopic camera viewfinder screen 72, previously discussed, with similar components labeled with the same reference numerals.

The face form camera viewfinder screen 106 may also be provided with a ghost image 108 upon activation of the ghost image icon 74. The face form ghost image 108 is similar to the ghost image 76, but is configured to approximate the top of the subject's head looking downward, as shown. A pair of spectacle frames may also appear in the ghost image 108.

The orientation indicator 78 is also provided on the face form viewfinder screen 106 and operates in a similar manner to that described for the pantoscopic angle measurements. The orientation indicator 78 is provided with orientation information from the orientation sensing unit 38, as previously discussed, and in the present example indicates a level or non-level horizontal position of the device 10.

The shutter-release icon 80 is also provided on the face form viewfinder screen 106 to actuate the camera unit 34 for capturing and storing an exposure. In taking the photo for the face form measurements, the subject may be instructed as to the proper position the subject should be in to perform the face form measurements. With respect to the face form measurements, the subject may be instructed to tilt their head downward while looking towards the floor so that a photo of the top of the subject's head may be taken from the side. Alternatively, a photo may be taken while the subject is seated or in a lowered position so that the user may be located at a position above the subject so that a photo of the top of the subject's head can be taken. When the subject's head is properly positioned within the viewfinder screen 106, as may be facilitated by the ghost image 108, the user may press or actuate the shutter-release icon 80 or 82. When the shutter-release is actuated, a face form preview screen (not shown), which may be similar to the preview screen 84 (FIG. 8) described for the pantoscopic angle, with an orientation prompt indication (e.g., the words "please level"), may be provided in the viewfinder screen 106 to prompt the user to orient the device 10 to the proper orientation, e.g., a level position, for taking of the subject's image to be used for face form measurements. The orientation indicator 78 provides information to the user to facilitate orienting the device 10 to the proper orientation. The user will then rotate or move the device 10, while the subject remains positioned in the viewfinder screen 106, until a level or proper orientation is achieved.

After the shutter-release icon 80 or other shutter-release controls are actuated, as soon as the device 10 is in the level or proper orientation, as measured by the orientation sensing unit 38, the camera unit 34 will automatically capture and store the image within the viewfinder screen 106 at the moment the orientation sensing unit 38 measures that the device 10 is at the selected orientation, e.g., a level position. This captured and stored image constitutes the image that may be used for the face form measurements. No images may be captured with the device 10 until the orientation sensing unit 38 measures that the selected orientation of the device 10 has been achieved after the shutter-release icon 80 or controls are actuated to actuate the camera unit 34. In this way, the user is assured that the captured image for the face form measurements are made at the precise orientation. This again removes any human error that may occur in orienting the device 10 to the selected orientation when the image is captured.

Once the image is captured, if the user is not satisfied with the photo as shown in the preview screen, the user may retake the photo of the subject's image. A retake photo icon, such as the icon 88 of FIG. 8, may be provided for this purpose to restart the image capturing process and the process may be repeated, as previously described. If the user is satisfied with the subject's image, the user saves and stores the image for use in face form measurements. A use-image icon, such as the use-image icon 92 of FIG. 8, may be provided to instruct the system 10 to store the captured image for use in making face form measurements.

Figure 13:
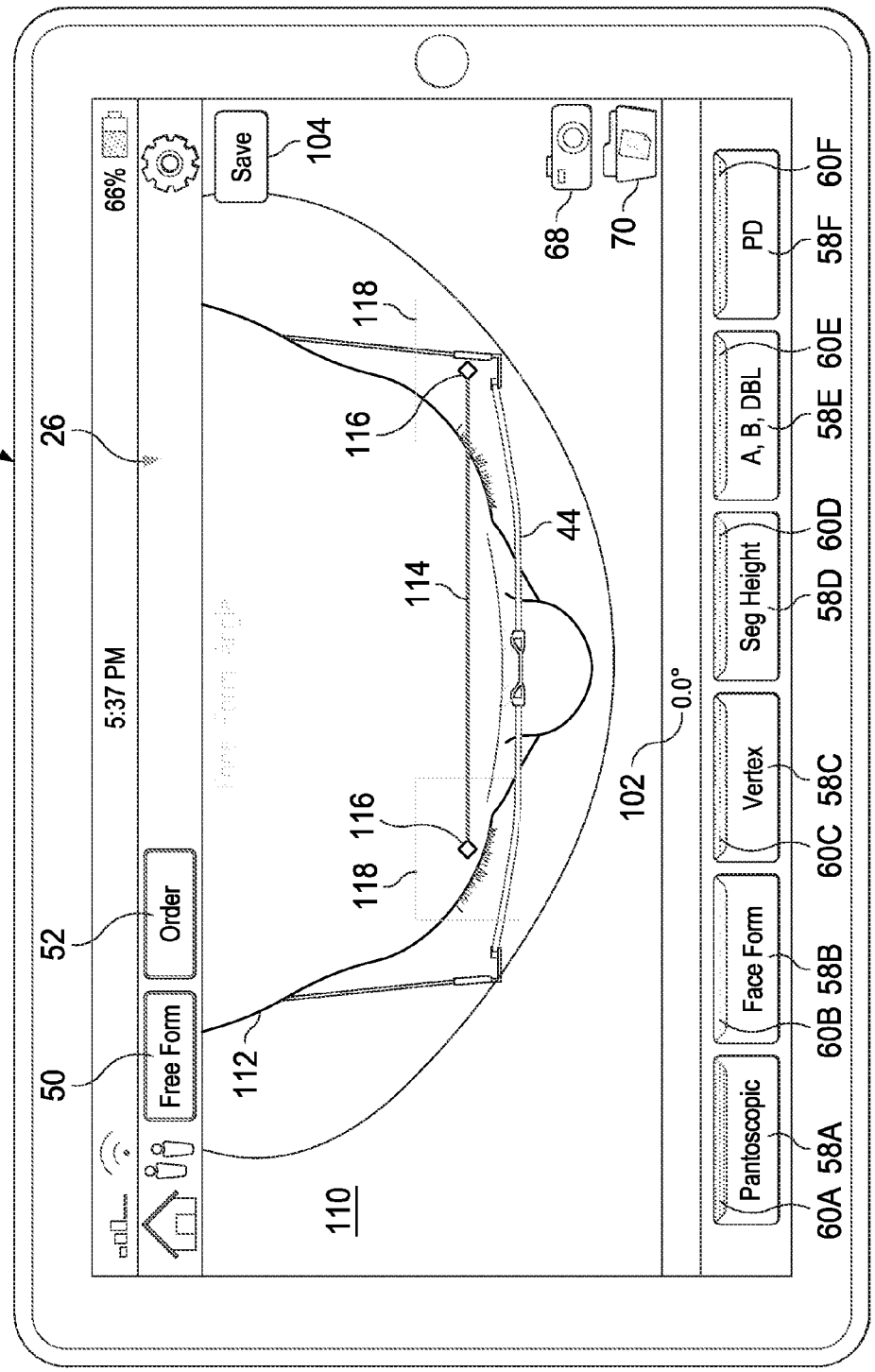
FIG. 13 is a plan view of a face form measurement screen of the display of the device of FIG. 4 shown with a captured image of the subject for use in performing face form measurements in accordance with an illustrative embodiment of the invention.

Upon storing of the captured face form image, the user may be taken to a face form measurement screen 110 where the face form image 112 is displayed, as shown in FIG. 13. Alternatively, a previously stored face form image may be retrieved from a photo file location of the system 10 by activating the file icon 70. With the face form image 112 presented in the face form measurement screen 110, the status bar 60B may be changed to a different appearance or color, e.g., orange, to indicate that the face form measurement is in process but not yet complete.

In the measurement screen 110, a straight line 114 having opposite endpoints or miers 116 and active areas 118, much like those of line 96 described for the pantoscopic measurements, is also generated and provided. The line 114 can be manipulated with the fingers or with a stylus in the same manner as the line 96, as previously described. When an active area 118 of one of the miers 116 is touched it may also change the appearance of the line 114, such as a change in color from red to green. This indicates that the line 114 is active and can be moved. The image 112 can also be moved or resized, if necessary, as previously discussed.

Figure 14:
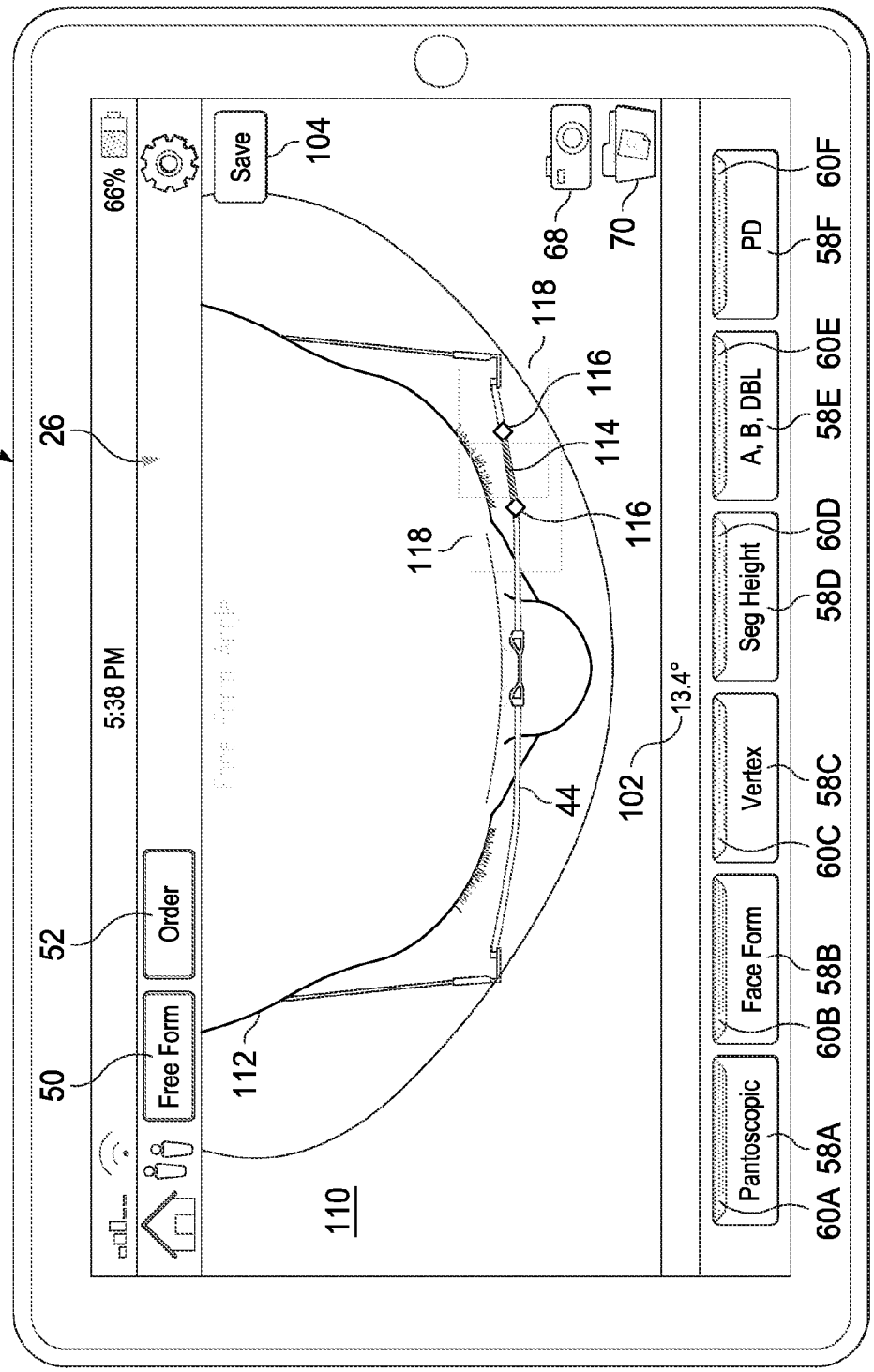
FIG. 14 is a plan view of a face form measurement screen of the display of the device of FIG. 13 shown with a face form measuring line in a position for measuring a face form angle in accordance with an illustrative embodiment of the invention.

Referring to FIG. 14, with the line 114 active, the line 114 is moved to a position on the top front of the spectacle frame 44 directly in front of the subject's pupil. The angle readout 102 may be displayed on the screen 110 to indicate the angle of the line 114. The face form angle is the angle of the plane of the lens (or frame) immediately in front of the subject's pupil as viewed from the top of the lens (or frame) relative to a horizontal line or axis, which represents the plane of the subject's face.

When the user is satisfied that the position of line 114, the user may activate the save icon 104, which saves the face form measurement. Saving may also include saving all or a portion of the information included on the face form measurement screen 110 at the moment the save icon 104 is activated. This may include the captured image 112, as well the final position of the line 114 over the frame 44, as well as the measured face form angle. In most instances, only one face form angle is measured, which is usually for the subject's left eye, although the face form angle for the opposite eye or both eyes may be measured with the system 10.

Figure 15:
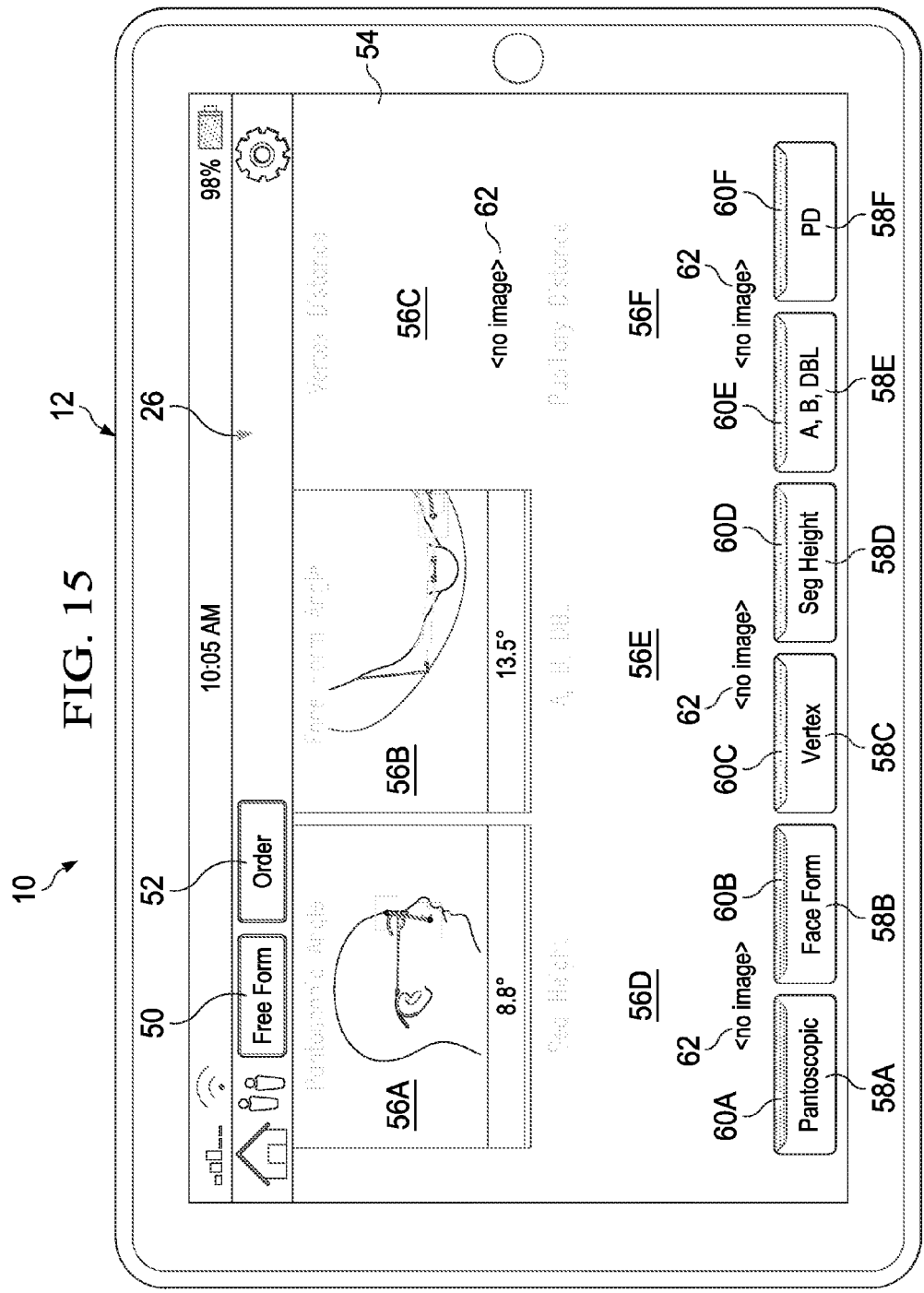
FIG. 15 is a plan view of the main measurement screen of the display of the device of FIG. 5 shown with a completed face form angle measurement quadrant in accordance with an illustrative embodiment of the invention.

Once the face form measurement is complete, the status bar 60B is changed in appearance to reflect this. The user is also presented with the main measurement screen 54, where the information from the face form measurement is now presented in quadrant 56B, as shown in FIG. 15. The user can then select from the remaining measurements to be completed by activating one of the quadrants 56C-56F or measurement icons 58C-58F.

To perform a vertex distance measurement, the quadrant 56C or icon 58C is actuated. This presents a vertex distance viewfinder screen 120, as shown in FIG. 16. The vertex distance viewfinder screen 120 may be similar to the viewfinder screens 72, 106, previously described, with similar components designated with the same reference numerals. A vertex distance ghost image 122 may be provided in the screen 120 by actuating the ghost image icon 74. The viewfinder screen 120 and ghost image 122 may be similar to the viewfinder screen 72 and ghost image 76 of a side profile of a human's head and face and may include an image of a pair of spectacle frames resting on the face.

To perform the vertex distance measurements, as well as other length measurements, a lock-on or reference device 124 is provided with the system 10, as shown in FIG. 17. The lock-on or reference device 124 is formed from a generally flat or planar body that includes one or more visually contrasting fields, such as the darkened fields 126, 128, that contrast with a background, such as the lighter background 130. Each of the fields 126 and 128 has known dimensions and serve as dimension references for particular measurements. In some embodiments, only a single field of known dimensions may be used. In the embodiment shown, the field 126 is a larger field of known dimensions, while the field 128 is smaller field of known dimensions. As an example, in the embodiment shown, the large contrasting field 126 is a rectangular field having a length of 90 mm and a width of 20 mm. The smaller rectangular field 128 has a length of 20 mm and width of 5 mm. Other dimensions for the fields 126, 128 may also be used. Other dimension reference devices or tools having known dimensions may also be used, however, provided they provide a dimension reference that can be viewed and seen in the photos and that is recognizable by computer implemented software or programs provided with the system 10.

As shown in FIG. 16, the ghost image 122 for the vertex distance measurement also contains a ghost image 130 of the lock-on device 124 positioned and oriented with the ghost image 122 of the subject where the actual lock-on device would generally be positioned and oriented when capturing the image of the subject.

When the user is ready to capture the image of the subject for the vertex distance measurements, the subject may be instructed as to the proper position the subject should be in to perform the vertex distance measurement. With respect to the vertex distance measurement, the subject may be instructed to look straight ahead holding their head level while holding the lock-on device 124 at a position so that it is near or resting along the side of the subject's head or face with the length of the smaller field 128 being held horizontally level. The user or optician may assist the subject in making sure the lock-on device 124 is properly positioned.

When the subject's profile is properly positioned with the lock-on device 124 within the viewfinder screen 120, as may be facilitated by the ghost image 122, the user may press or actuate the shutter-release icon 80 or 82. When the shutter-release is actuated, a vertex distance preview screen (not shown), which may be similar to the preview screen 84 (FIG. 8) described for the pantoscopic angle, with an orientation prompt indication (e.g., the words "please level"), may be provided in the viewfinder screen 120 to prompt the user to orient the device 10 to the proper orientation, e.g., a level position, for taking of the subject's image to be used for vertex distance measurements. The orientation indicator 78 provides information to the user to facilitate orienting the device 10 to the proper orientation. The user will then rotate or move the device 10, while the subject remains positioned in the viewfinder screen 120, until a level or proper orientation is achieved.

After the shutter-release icon 80 or 82 is actuated, as soon as the device 10 is in the selected orientation, as measured by the orientation sensing unit 38, the camera unit 34 will automatically capture and store the image within the viewfinder screen 120 at the moment the orientation sensing unit 38 measures that the device 10 is at the selected orientation, e.g., a level position. This captured image constitutes the image that may be used for the vertex distance measurements. In this way, the user is assured that the captured image for the face form measurements are made at the precise orientation. This again removes any human error that may occur in orienting the device 10 to the selected orientation when the image is captured.

Once the image is captured, if the user is not satisfied with the photo as shown in the preview screen, the user may retake the photo of the subject's image, as previously described. If the user is satisfied with the subject's image, the user saves and stores the image for use in vertex distance measurements. A use-image icon, such as the use-image icon 92 of FIG. 8, may be provided to instruct the system 10 to store the captured image for use in making the vertex distance measurements.

Figure 18:
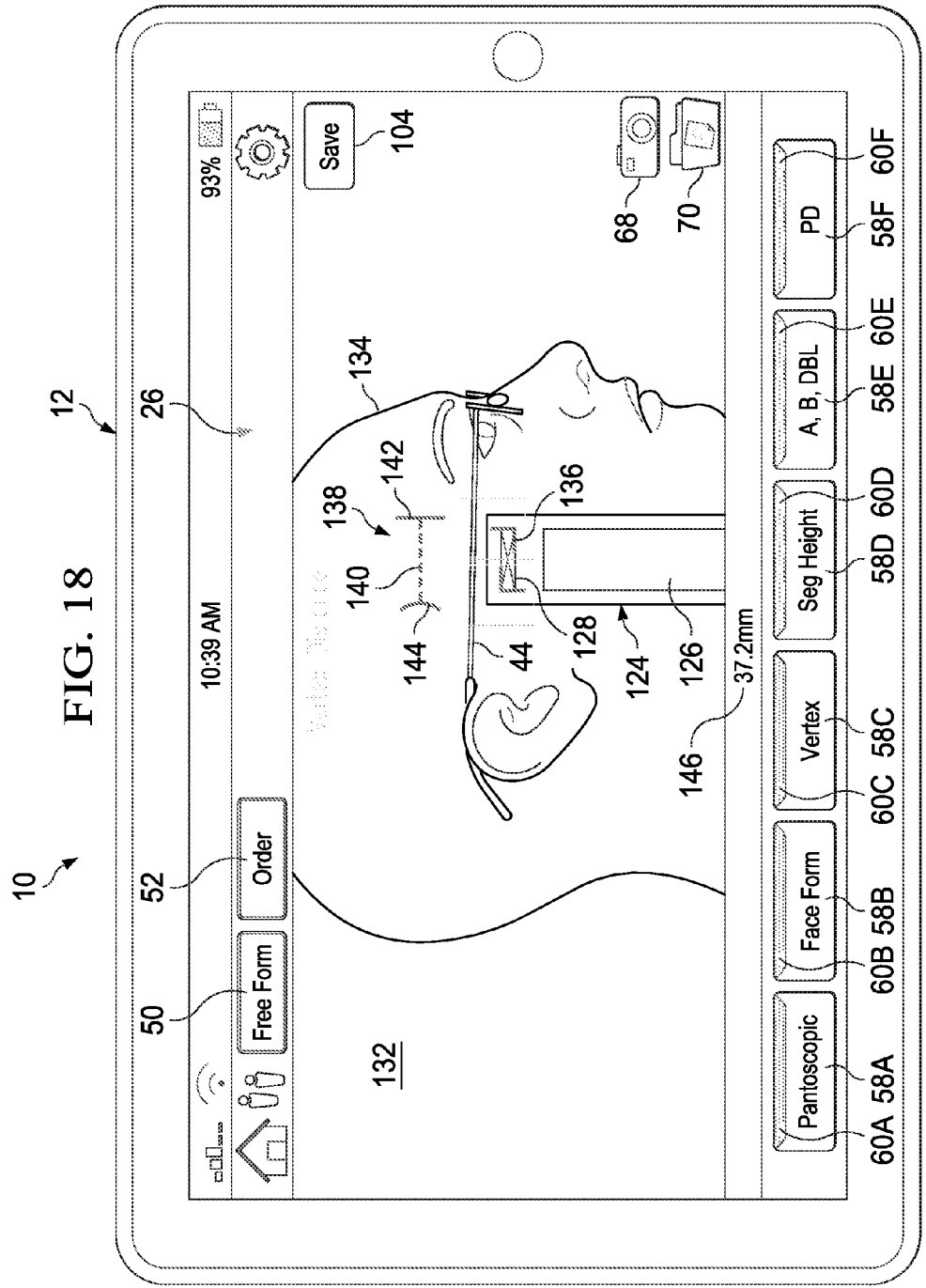
FIG. 18 is a plan view of a vertex distance measurement screen of the display of the device of FIG. 4 shown with a captured image of the subject for use in performing vertex distance measurements in accordance with an illustrative embodiment of the invention.

Upon storing of the captured vertex distance measurement image, the user may be taken to a vertex distance measurement screen 132 where the captured and stored vertex distance image 134 is displayed in the display 26 of the device 10, as shown in FIG. 18. Alternatively, a previously stored vertex distance image may be retrieved from a photo file location of the system 10 by activating the file icon 70. With the vertex distance image 134 presented in the measurement screen 132, the status bar 60C may be changed to a different appearance or color, e.g., orange, to indicate that the vertex distance measurement is in process but not yet complete.

In the measurement screen 132, the image of the lock-on device 124 held by the subject will also appear in the image 134. By tapping in the area of the smaller darkened field 128 of the lock-on device 124, a lock-on icon 136 is presented. The icon 136 may fill all or a portion of the image of field 128. The lock-on icon 136 may be a box, X, change in color, or combination of such features, or other feature or representation or prompt that indicates to the user that the system 10 has recognized the field 128 as the dimension reference for the vertex distance measurement. The processing system 14 of the device 10 is provided with a program, software, system or unit to provide this function. This may consist of image recognition software that recognizes certain features or aspects of or within images. In the present invention, such software may provide recognition of a contrasting or darkened field, which may be rectangular in shape. This can be fine tuned or adjusted to recognize the features of the dimension reference device 124, such as the darkened rectangular fields 126, 128.

By tapping the darkened field 128 so that the lock-on icon 136 appears in the field 128, the user is confirming for the system 10 that this is the feature that represents a length of 20 mm, for the particular example presented. Thus, the system 10 can now calculate the length of objects or be used for measuring spatial dimensions within the same or substantially the same plane as the plane of the field 128 using it as a point of reference for scale, length, size or spatial dimensions.

In the vertex distance measurement screen 132, a vertex distance measuring device 138 is provided. In the embodiment shown in FIG. 18, the measuring device 138 is in the form of a horizontal straight line 140 with endpoints or miers 142, 144. As presented in FIG. 18, the left mier 142 is configured as an arcuate line in the form of a quarter circle with the apex of the circle touching the end of line 140. The mier 142 could also constitute a straight vertical line, or other configuration, or it may merely be an endpoint of the line 140 where the line 140 terminates. The arcuate mier 142, however, prompts and facilitates positioning and aligning of the mier 142 with the curved cornea of the subject's eye. The right mier 144 constitutes a straight vertical line, although it could have different configurations as well, including being merely an endpoint of the line 140. Active areas, such as those described for the active areas 100, 118, may be provided around the miers 142, 144. When an active area around one of the miers 142, 144 is touched it may also change in appearance of the miers 142, 144 or line 140, such as a change in color from red to green. This indicates that the line 140 or miers 142, 144 is active and can be moved. The image 134 can also be moved or resized, if necessary, as previously discussed.

Figure 19:
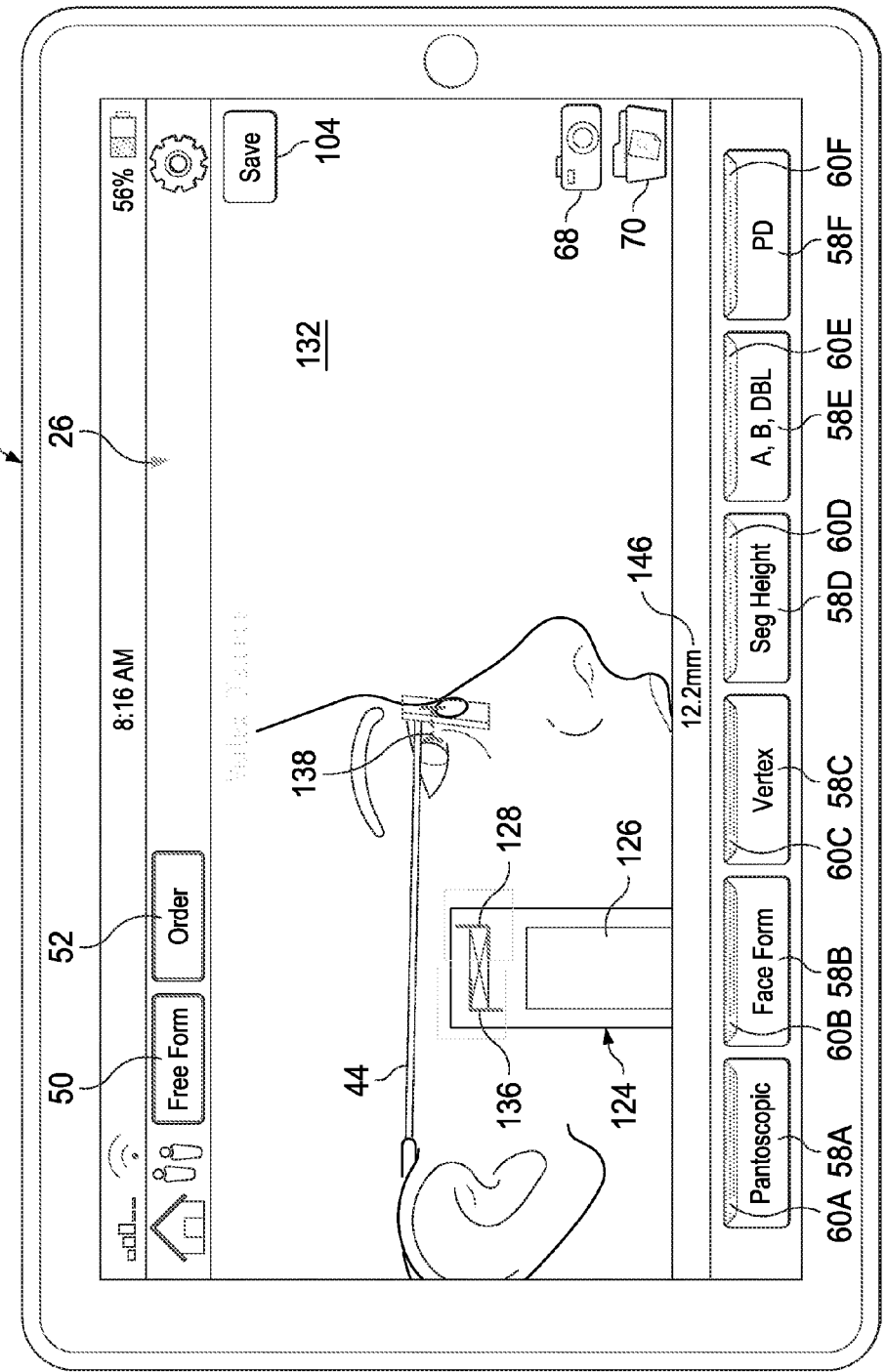
FIG. 19 is a plan view of the vertex distance measurement screen of FIG. 18 shown with an enlarged area of the captured image of the subject for use in performing vertex distance measurements in accordance with an illustrative embodiment of the invention.

Referring to FIG. 19, with the miers 142, 144 active, the line 140 is moved to a position where the mier 142 aligns with the subject's cornea and the mier 144 aligns with the back portion of the lens or plane of the frame 44 immediately in front of the cornea, as is shown. A vertex distance measurement readout 146 may be displayed on the screen 132 to indicate the length of the line 140, which corresponds to the vertex distance as calculated with the system 10 based upon the known length of the reference field 128.

When the user is satisfied that the position of vertex distance measuring device 138, the user may activate the save icon 104, which saves the vertex distance measurement. Saving may also include saving all or a portion of the information included on the vertex distance measurement screen 132 at the moment the save icon 104 is activated. This may include the captured image 134, as well the final position of the vertex distance measuring device 138 and the vertex distance measurement. In most instances, only one vertex distance is measured for one eye, although the vertex distance for the opposite eye or both eyes may be measured with the system 10, using a similarly captured image for the other eye.

Figure 20:
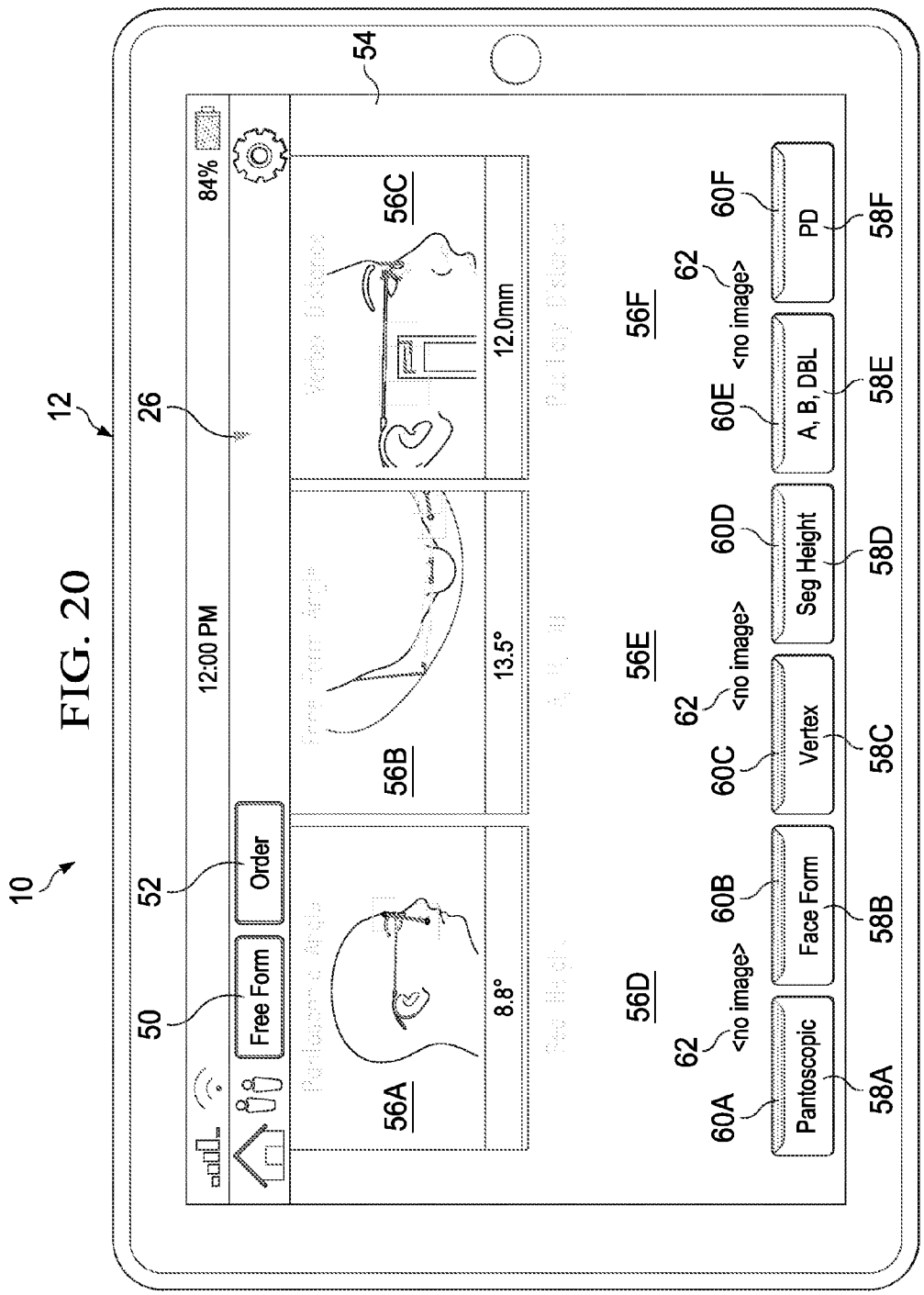
FIG. 20 is a plan view of the main measurement screen of the display of the device of FIG. 5 shown with a completed vertex distance measurement quadrant in accordance with an illustrative embodiment of the invention.

Once the vertex distance measurement is complete, the status bar 60C is changed in appearance to reflect this. The user is also presented with the main measurement screen 54, where the information from the vertex distance measurement is now presented in quadrant 56C, as shown in FIG. 20. The user can then select from the remaining measurements to be completed by activating one of the quadrants 56D-56F or measurement icons 58D-58F.

Figure 21:
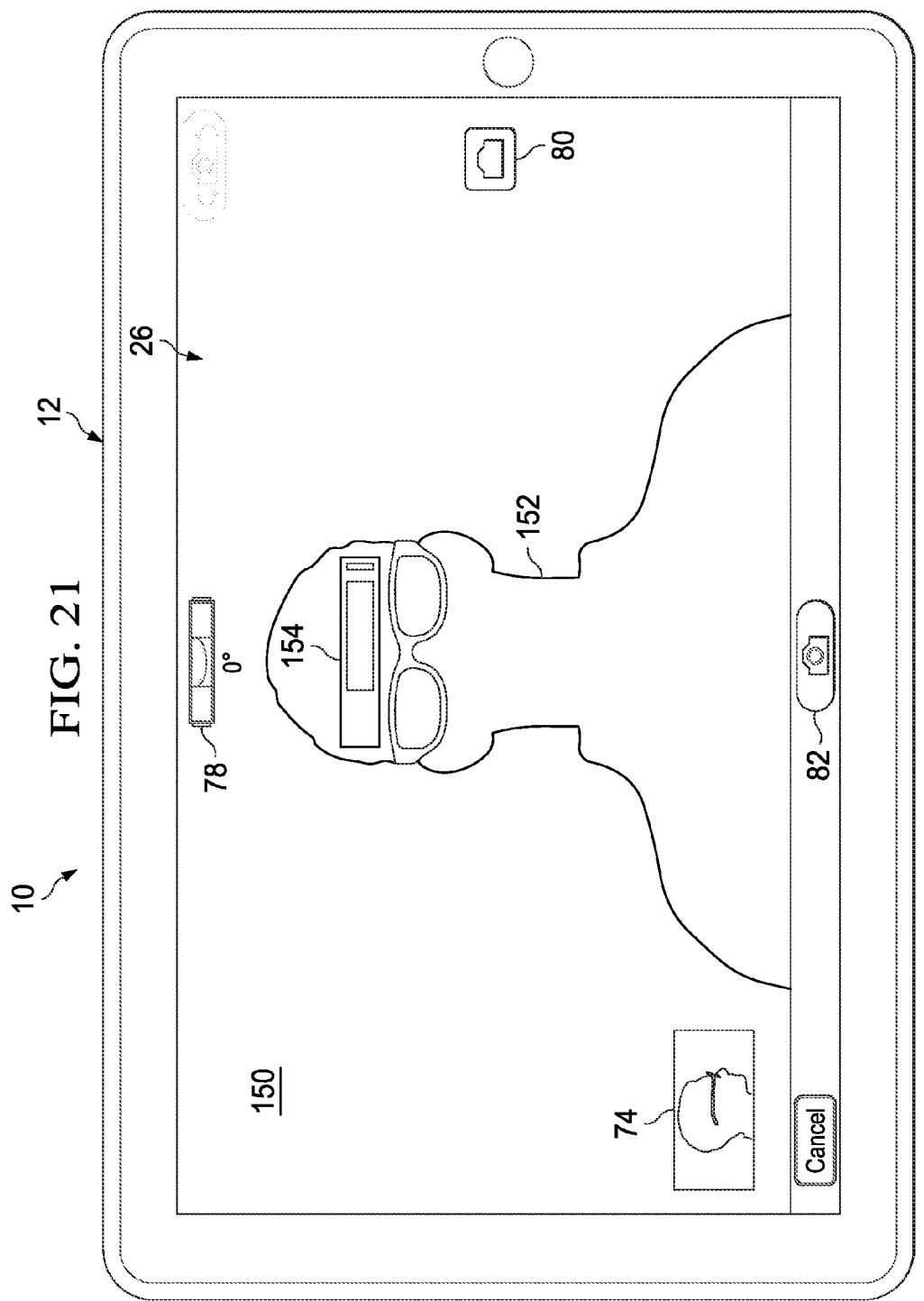
FIG. 21 is a plan view of a viewfinder screen of the display of the device of FIG. 4 shown with a ghost image for seg height and other measurements in accordance with an illustrative embodiment of the invention.

For seg height measurements, spectacle frame dimension measurements (e.g., A, B, DBL) and pupillary distance measurements the same captured image may be used for all such measurements. To perform these measurements, the user may activate quadrant 56D or icon 58D for seg height measurement, although any of the other quadrants 56E or 56F, or corresponding measurement icons 58E, 58F may also be activated. If no image for these measurements has been previously captured for these measurements, the system 10 will know that this is the case and an image capturing screen will be provided. In the present example, actuating the quadrant for seg height measurement will present a viewfinder screen 150, as shown in FIG. 21. The viewfinder screen 150 may be similar to the viewfinder screens 72, 106, 120 previously described, with similar components designated with the same reference numerals. A ghost image 152 may be provided in the screen 150 by actuating the ghost image icon 74. The ghost image 152 presented in screen 150 is that of a human's head facing forward or towards the user and may include an image of a pair of spectacle frames resting on the face.

As shown in FIG. 21, the ghost image 152 also contains a ghost image 154 of the lock-on device 124 positioned and oriented with the ghost image 152 of the subject where the actual lock-on device 124 would be positioned and oriented when capturing the image of the subject.

When the user is ready to capture the image of the subject for the remaining measurements, the subject may be instructed as to the proper position the subject should be in to perform the vertex distance measurement. With respect to such measurement, the subject may be positioned approximately arm's length away from the user and be instructed to look straight ahead holding their head level while holding the lock-on device 124 at a position just above the subject's eyeglass frames with the lock-on device 124 being held so that the length of the larger field 126 is oriented horizontally, as shown by the ghost image 154. The user or optician may assist the subject in making sure the lock-on device 124 is properly positioned. The picture is taken with the camera lens 36 centered and focused on the center of the bridge of the subject's nose.

When the subject is properly positioned with the lock-on device 124 within the viewfinder screen 150, as may be facilitated by the ghost image 152, the user may press or actuate the shutter-release icon 80 or 82. When the shutter-release is actuated, a preview screen (not shown), which may be similar to the preview screen 84 (FIG. 8) described for the pantoscopic angle, with an orientation prompt indication (e.g., the words "please level"), may be provided in the viewfinder screen 150 to prompt the user to orient the device 10 to the proper orientation, e.g., a level position, for taking of the subject's image to be used for remaining measurements. The orientation indicator 78 provides information to the user to facilitate orienting the device 10 to the proper orientation. The user will then rotate or move the device 10, while the subject remains positioned in the viewfinder screen 150, until a level or proper orientation is achieved.

After the shutter-release icon 80 or 82, other shutter-release controls are actuated, as soon as the device 10 is in the selected orientation, as measured by the orientation sensing unit 38, the camera unit 34 will automatically capture and store the image within the viewfinder screen 150 at the moment the orientation sensing unit 38 measures that the device 10 is at the selected orientation, e.g., a level position. This captured and stored image constitutes the image that may be used for the remaining measurements. In this way, the user is assured that the captured image for the remaining measurements is made at the precise orientation. This again removes any human error that may occur in orienting the device 10 to the selected orientation when the image is captured.

Once the image is captured, the user may retake or save the photo of the subject's image, as previously described.

Figure 22:
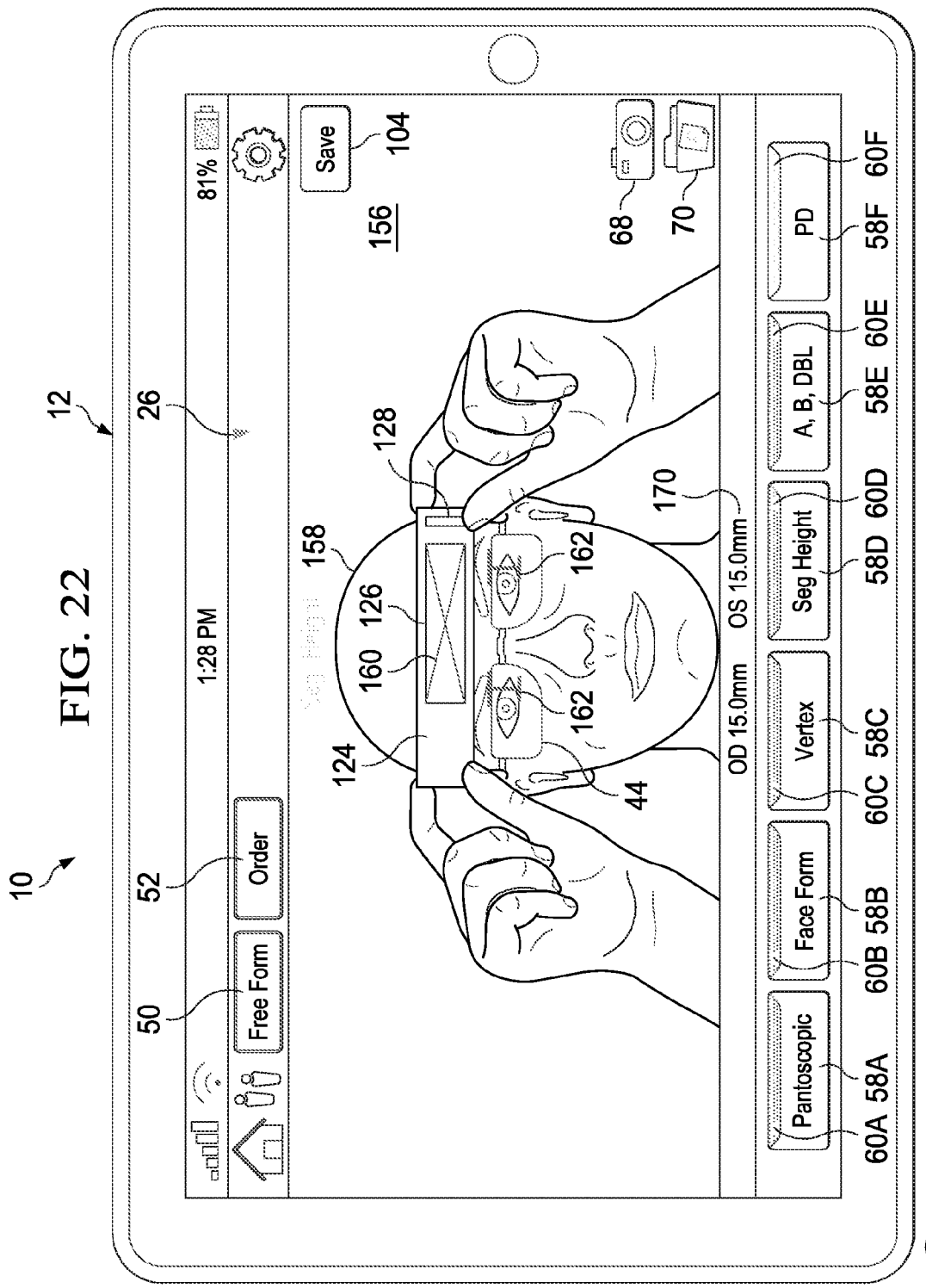
FIG. 22 is a plan view of a seg height measurement screen of the display of the device of FIG. 4 shown with a captured image of the subject for use in performing seg height measurements in accordance with an illustrative embodiment of the invention.

Upon storing of the captured image, the user is taken to a seg height measurement screen 156 where the captured and stored image 158 is displayed in the display 26 of the device 10, as shown in FIG. 22. Alternatively, a previously stored image may be retrieved from a photo file location of the system 10 by activating the file icon 70. With the image 158 presented in the measurement screen 156, the status bar 60D may be changed to a different appearance or color, e.g., orange, to indicate that the seg height measurement is in process but not yet complete.

In the measurement screen 156, the image of the lock-on device 124 will also appear in the image 158. By tapping in the area of the large darkened field 126 of the image of lock-on device 124, a lock-on icon 160 is presented. The icon 160 may be similar to and function similarly to the lock-on icon 136, as previously described. By tapping the image of the darkened field 126, the lock-on icon 160 that appears in the field 126, the user is confirming for the system 10 that this is the feature that represents a length of 90 mm, for the particular example presented. Thus, the system 10 can now calculate the length or size of objects within the same or substantially the same plane as the plane of the field 126 using the field 126 as a point of reference for length or size.

In the seg height measurement screen 156, a pair of seg height measuring devices 162 is provided for the left and right eyes of the subject. In the embodiment shown (FIG. 22), the measuring devices 162 are each in the form of a vertical straight line 164 with opposite upper and lower endpoints or miers 166, 168, which are each configured as horizontal line segments. The miers 166, 168 could be provided in other configurations, or it may merely be the endpoints of the line 164 where the line 164 terminates. Active areas, such as those described for the active areas 100, 118, may be provided around the miers 166, 168.

Figure 23:
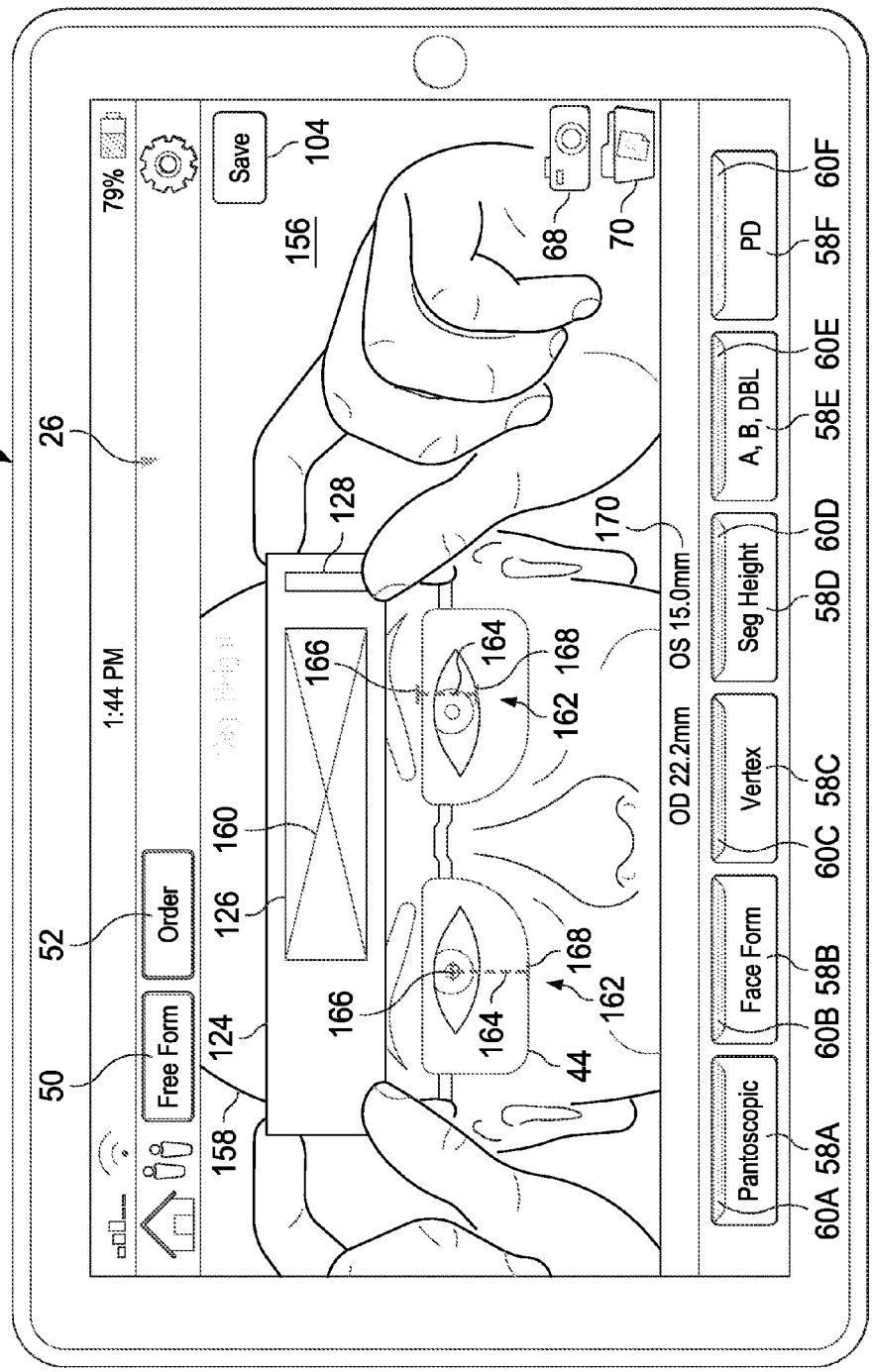
FIG. 23 is a plan view of the seg height measurement screen of FIG. 22 shown with an enlarged area of the captured image of the subject for use in performing seg height measurements in accordance with an illustrative embodiment of the invention.

In measuring the seg height for each eye, the active area around the lower mier 168, is touched so that it may be repositioned. The mier 168 may also change in appearance, such as a change in color from red to green. This indicates that the line 168 is active and can be moved. The image 158 can also be moved or resized, if necessary, as previously discussed. The mier 168 of the device 162 for each eye is positioned at the bottom of the frame 44 below the center of the subject's pupil, as shown for the subject's right eye in FIG. 23. The upper mier 166 for each eye is also activated and positioned at the center of the subject's pupil. Once so positioned, the length of the vertical lines 164 corresponds to the seg height for each of the subject's eyes as calculated with the system 10 based upon the known length of the reference field 126. A seg height measurement readout 170 for the seg height for the oculus dexter (OD) or right eye and the oculus sinister (OS) or left eye may be displayed on the screen 156.

When the user is satisfied that the measurement devices 162 are properly positioned, the user may activate the save icon 104, which saves the seg height measurements. Saving may also include saving all or a portion of the information included on the seg height measurement screen 156 at the moment the save icon 104 is activated. This may include the captured image 115, as well the final position of the seg height measurement devices 162 and the seg height measurements.

Once the seg height measurements are complete, the status bar 60D is changed in appearance to reflect this. The user is also presented with the main measurement screen 54, where the information from the seg height measurements is presented in quadrant 56D. The user can then select from the remaining measurements to be completed by activating one of the quadrants 56E-56F or measurement icons 58E-58F.

Figure 24:
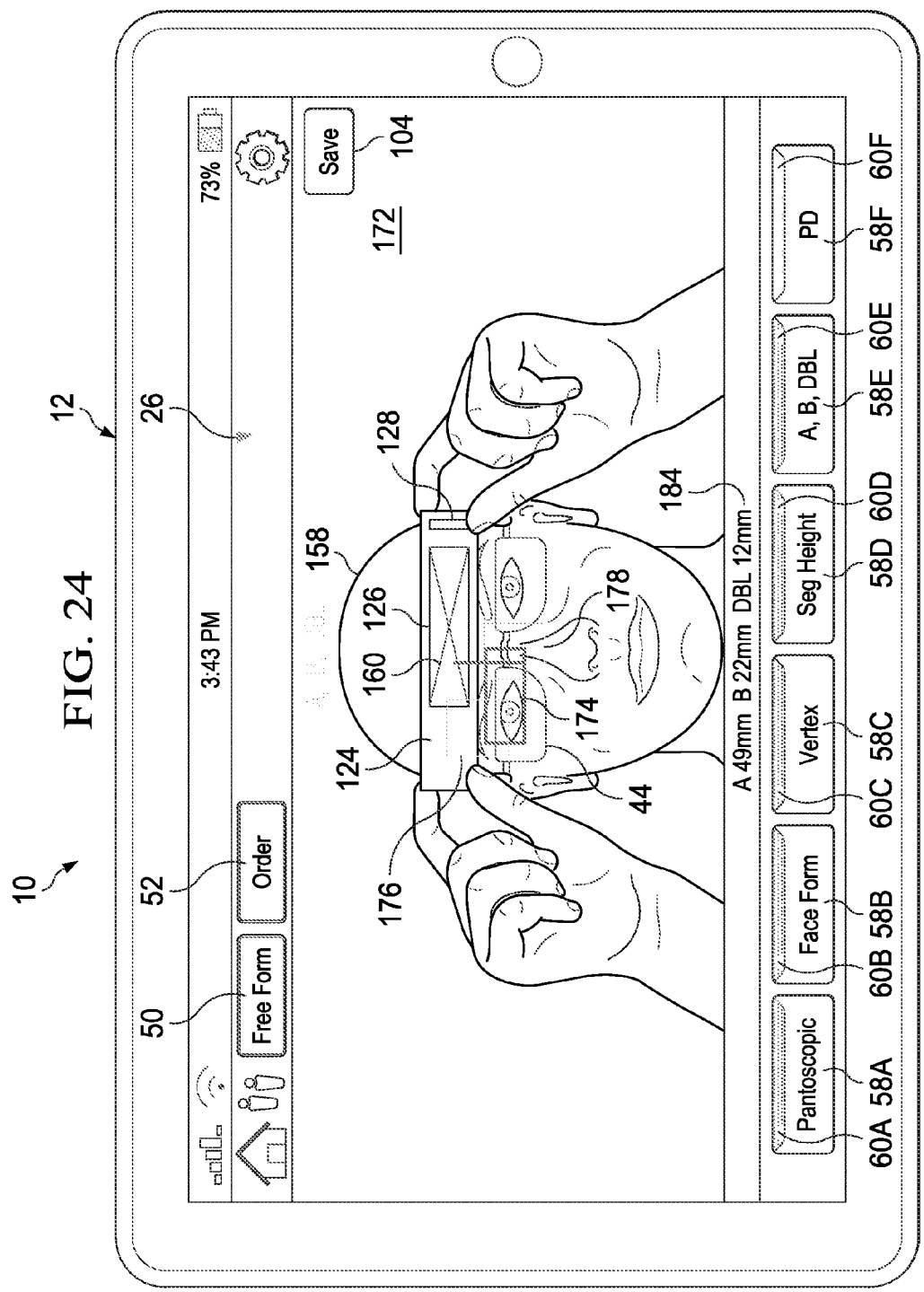
FIG. 24 is a plan view of spectacle frame measurement screen of the display of the device of FIG. 4 shown with a captured image of the subject for use in performing spectacle frame measurements in accordance with an illustrative embodiment of the invention.

To perform the spectacle frame dimension measurements, the same captured image for the previous seg height measurement is used. In the present example, measured dimensions are the A-dimension, which is the horizontal width of the frame or lens; the B-dimension, which is the depth or vertical dimension of the frame or lens; and the DBL-dimension, which is the minimum horizontal distance between the frames or lenses. It should be understood that other frame measurements can also be made with the device, such as DBC (distance between centers), ED (effective diameter), G (geometric center) dimensions, as well as others. To perform the A, B, and DBL measurements, the user activates quadrant 56E or icon 58E. This presents the previously stored image 158 in a spectacle frame dimension measurement screen 172 in the display 26 of the device 10, as shown in FIG. 24. With the image 158 presented in the measurement screen 172, the status bar 60E may be changed to a different appearance or color, e.g., orange, to indicate that the spectacle frame dimension measurements are in process but not yet complete.

In the measurement screen 172, the image of the lock-on device 124 will also appear in the image 158. The lock-on icon 160 may be absent, however, as the dimension reference information has already been stored and is being used for the additional measurements.

Figure 25:
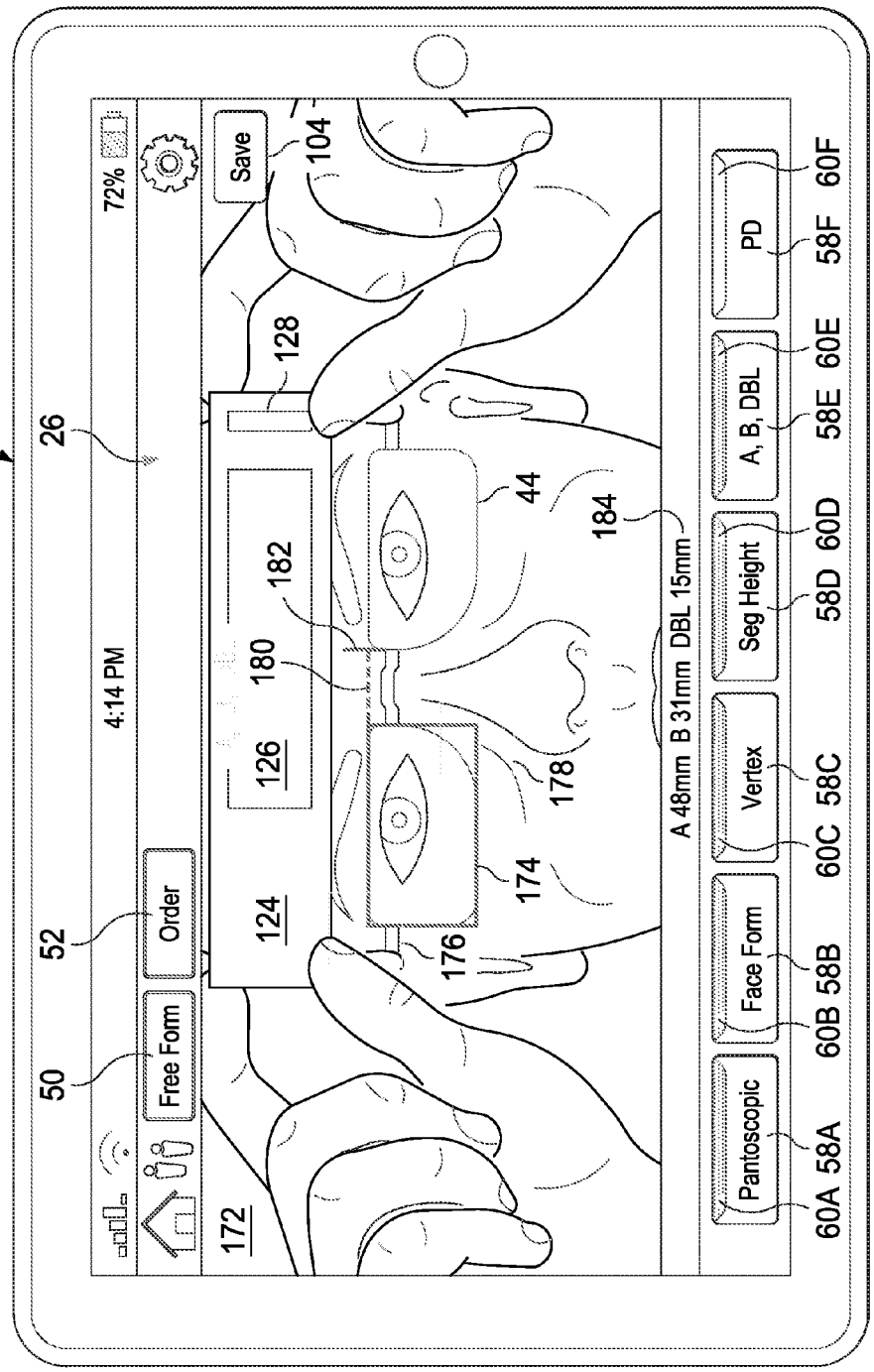
FIG. 25 is a plan view of the spectacle frame measurement screen of FIG. 24 shown with an enlarged area of the captured image of the subject for use in performing spectacle frame measurements in accordance with an illustrative embodiment of the invention.

In the frame dimension measurement screen 172, a measuring device 174 in the form of rectangular box formed from horizontal upper and lower sides and opposite vertical left and right sides is presented, as shown in FIG. 25. Tapping or activating active areas 176, 178 provided around opposite corners of the box 174 facilitate positioning, sizing and adjustment of the box 174. The active areas of the box corners may also change in appearance when activated, such as a change in color from red to green. This indicates that the corners are active and can be moved. The image 158 can also be moved or resized, if necessary, as previously discussed. The box 174 is usually positioned around the frame or lens of the subject's right eye, although the left eye may also be used. The box 174 is sized and positioned so that it overlays the outer perimeter of the lens or the perimeter where the lens meets the frame 44. This facilitates measuring of the A and B dimensions.

An arm or extension 180 in the form a straight horizontal line extending from the upper right edge of the box 174 is also provided. The line 180 terminates in an endpoint or miers 182, which is shown as a vertical line segment, although other configurations for the mier 182 may be used. An active area may be provided around the miers 182 to facilitate positioning and sizing of the line 180. Touching of the active area around the miers 182 may also cause it to change in appearance to indicate it is active. The mier 182 is positioned so that it extends to the outer perimeter of the other lens or frame opening along the bridge of the subject's nose. This facilitates measuring of the DBL dimension.

A frame measurement readout 184 may be displayed on the screen 172 to indicate the various measurements A, B, and DBL, which corresponds to the distances as calculated with the system 10 based upon the known length of the reference field 126.

When the user is satisfied with the positioning of the box 174 and arm 180 for the frame measurements, the user may activate the save icon 104, which saves the frame measurements. Saving may also include saving all or a portion of the information included on the frame measurement screen 172 at the moment the save icon 104 is activated. This may include the captured image 158, as well the final position of the box 174 and arm 180 and the frame measurements.

Figure 26:
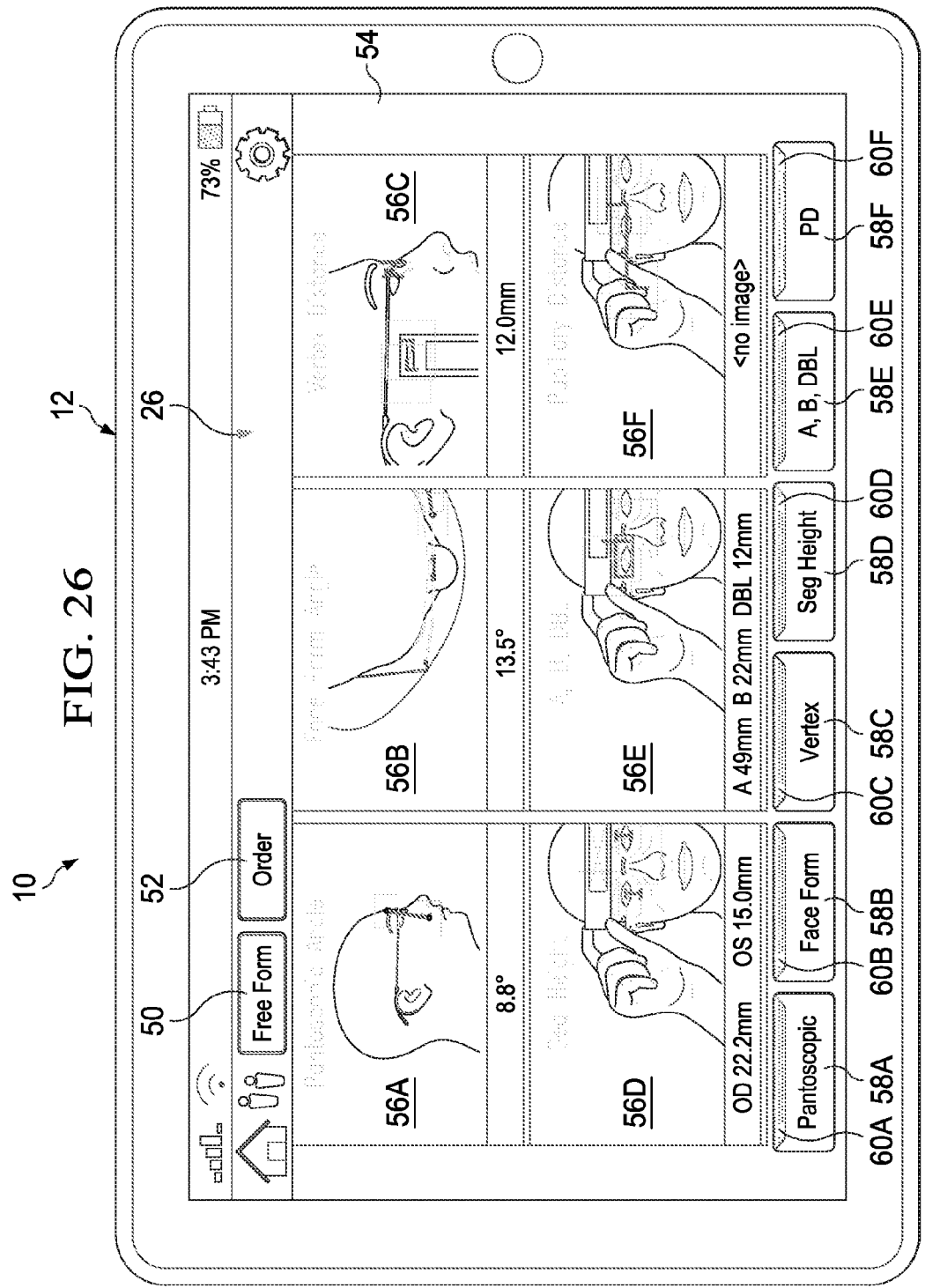
FIG. 26 is a plan view of the main measurement screen of the display of the device of FIG. 5 shown with a completed spectacle frame measurement quadrant in accordance with an illustrative embodiment of the invention.

Once the frame measurements are complete, the status bar 60E is changed in appearance to reflect this. The user is also presented with the main measurement screen 54, where the information from the frame measurements is presented in quadrant 56E, as shown in FIG. 26. The user can then select the remaining measurement to be completed by activating the quadrant 56F or measurement icons 58F for pupillary distance.

Figure 27:
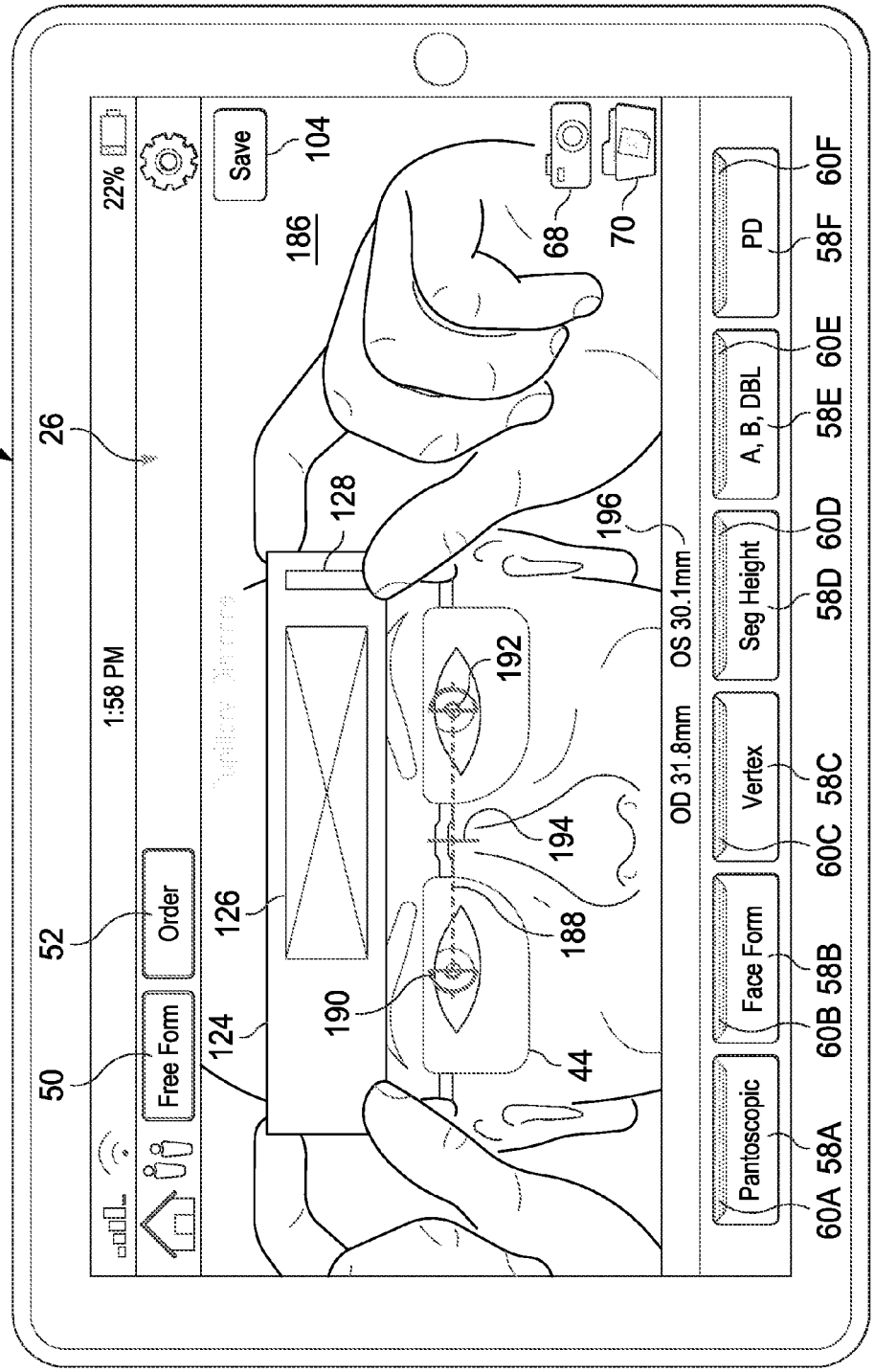
FIG. 27 is a plan view of pupillary distance (PD) measurement screen of the display of the device of FIG. 4 shown with a captured image of the subject for use in performing pupillary distance measurements in accordance with an illustrative embodiment of the invention.

To measure pupillary distance (PD), the same captured image 158 for the previous seg height measurement is used. In the example shown, pupillary distance is the distance between the subject's pupils as measured from the center of the pupils. Upon activating quadrant 56F or icon 58F, the previously stored image 158 in a pupillary distance measurement screen 186 is presented in the display 26 of the device 10, as shown in FIG. 27. With the image 158 presented in the measurement screen 186, the status bar 60F may be changed to a different appearance or color, e.g., orange, to indicate that the spectacle frame dimension measurements are in process but not yet complete.

In the measurement screen 186, the image of the lock-on device 124 will also appear in the image 158. The lock-on icon 160 may be absent, however, as the dimension reference information has already been stored and is being used for the additional measurements.

Figure 28:
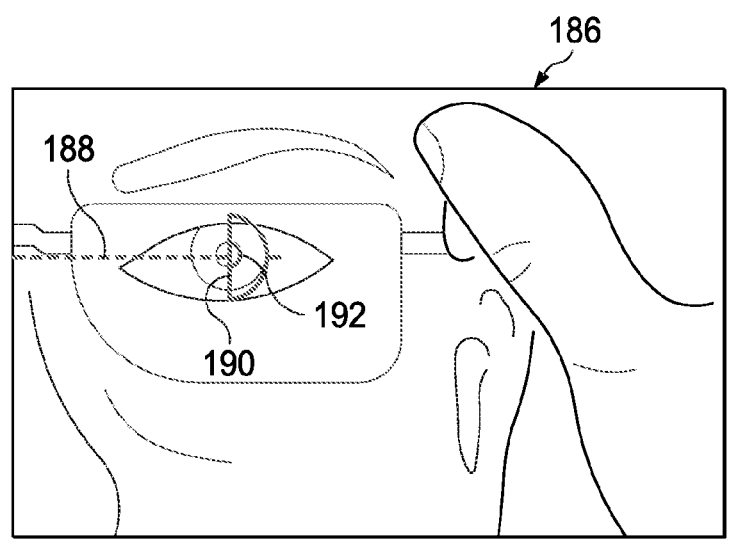
FIG. 28 is a plan view of an enlarged portion of the pupillary distance measurement screen of FIG. 27 showing details of the pupillary distance measurement device in accordance with an illustrative embodiment of the invention.

In the pupillary distance measurement screen 186, a measuring device 188 in the form of straight horizontal line is presented. The end points or miers at the ends of the line 188 are in the form of two concentric semicircles 190, 192 that approximate the outer extent of the iris and pupil of a subject's eye, respectively, as shown in FIG. 28. Other configurations for the miers 190, 192 may also be provided. Tapping or activating active areas around the miers 190, 192, such as those previously described, facilitate positioning, sizing and adjustment of the measuring device 188. A center vertical line 194 is also provided at the center of the measuring device 188 and is provided with active areas to activate the vertical line 194 so that it may be moved along the length of the horizontal line 188. The miers 190, 192 and line 194 may also change in appearance when activated, such as a change in color from red to green. This indicates that the miers 190, 192 and line 194 are active and can be moved. The image 158 can also be moved or resized, if necessary, as previously discussed. The measuring device 188 is positioned so that the vertical line forming the diameter of each semi-circular mier 190, 192 is positioned in the center of the subject's pupil, as shown in FIG. 28. The vertical line 194 is moved as necessary so that is positioned at the center bridge of the frame 44 (FIG. 27). This facilitates measuring of the pupillary distance. A pupillary distance readout 196 may be displayed on the screen 186 to indicate the pupillary distance, which corresponds to the distances as calculated with the system 10 based upon the known length of the reference field 126.

When the user is satisfied that the positioning of the line 188, the user may activate the save icon 104, which saves the pupillary distance measurement. Saving may also include saving all or a portion of the information included on the pupillary distance measurement screen 186 at the moment the save icon 104 is activated. This may include the captured image 158, as well the final position of the measuring device 188 and the pupillary distance measurements.

Figure 29:
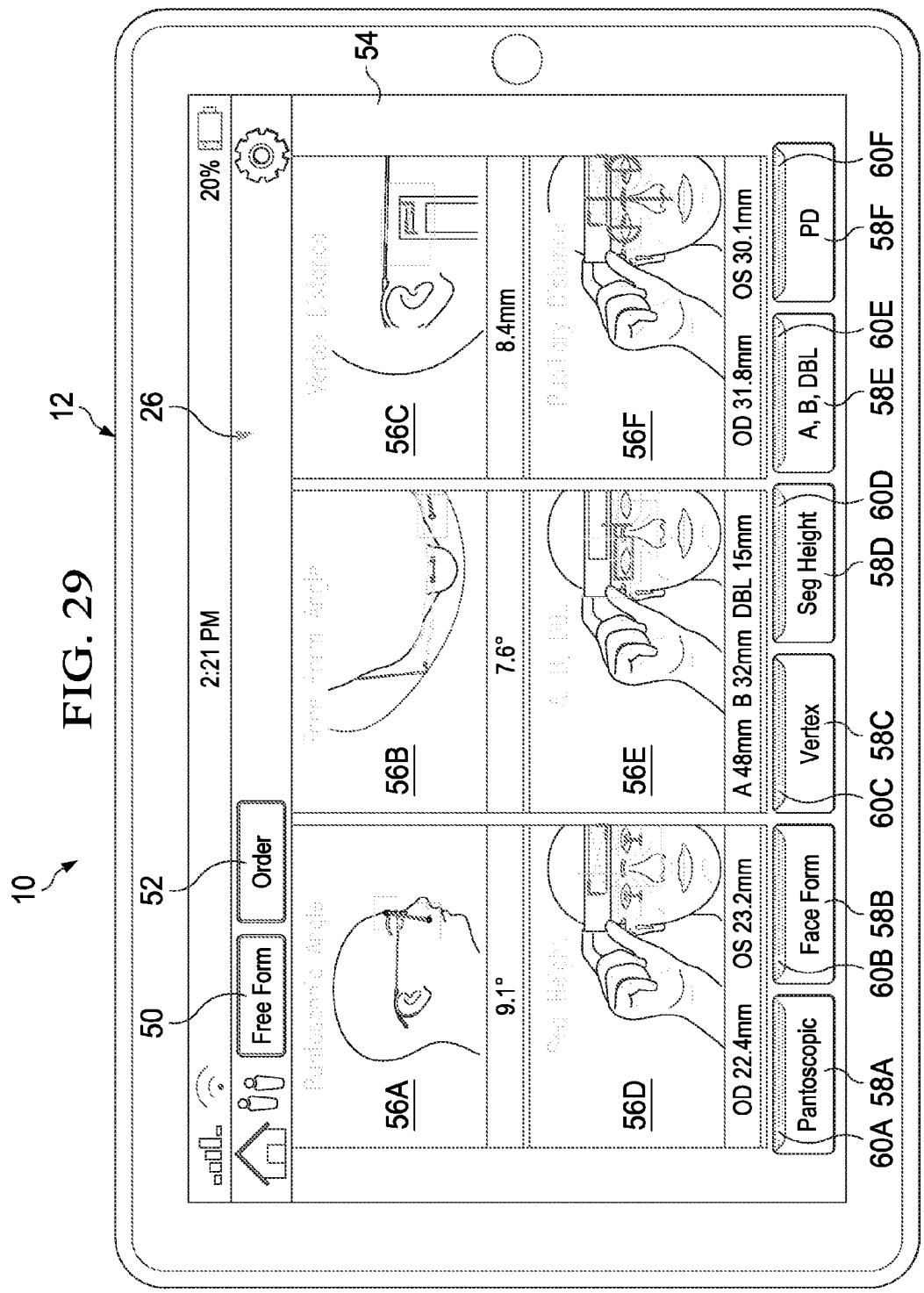
FIG. 29 is a plan view of the main measurement screen of the display of the device of FIG. 5 shown with a completed pupillary distance measurement quadrant in accordance with an illustrative embodiment of the invention.

Once the frame measurements are complete, the status bar 60F is changed in appearance to reflect this. The user is also presented with the main measurement screen 54, where the information from the pupillary measurements is presented in quadrant 56F, as shown in FIG. 29. The user can now also see that all the measurements for all the quadrants 56A-56F are now complete, as indicated by the appearance of the icons 58A-58F.

The measurements taken with the system 10 can now be used in ordering the final lenses and eyeglasses. The user may activate the ordering icon 52 located on the main screen 54. The ordering icon 52 may be located on other screens of the device 10, as well.

Figure 30:
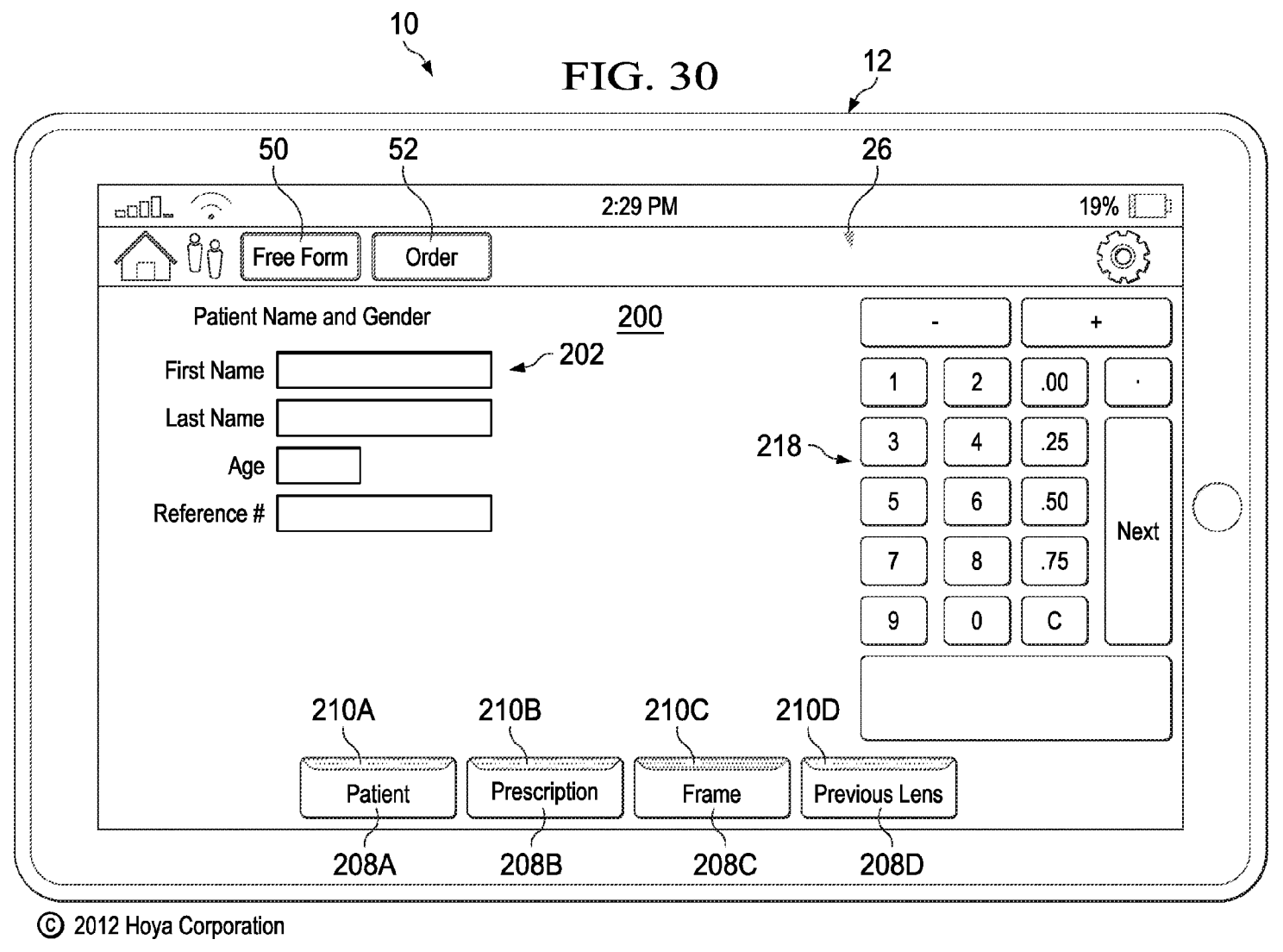
Figure 31:
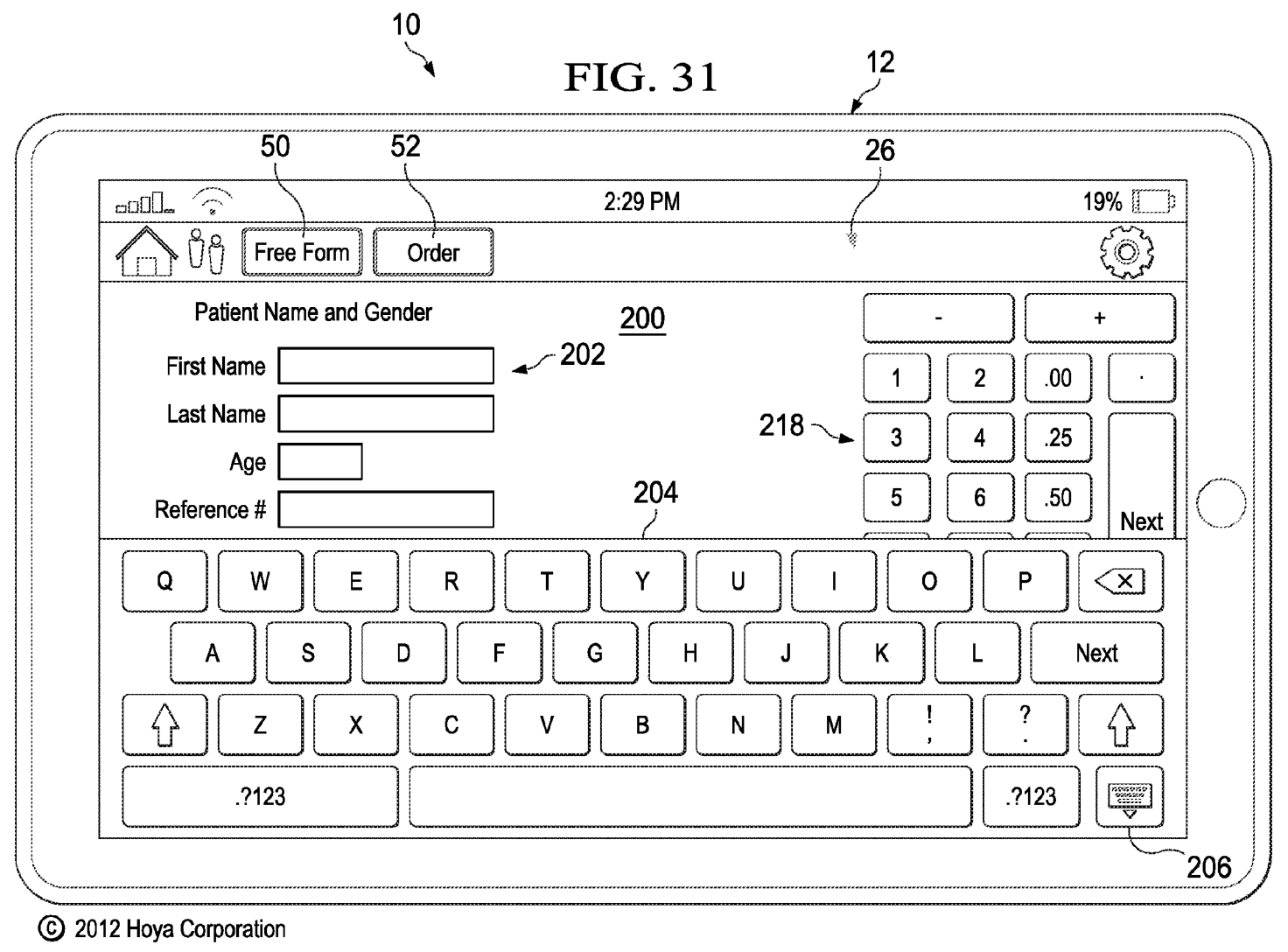

When the ordering icon 52 is activated, a subject or patient data entry screen 200 may initially presented in the display 26 of the device 10, as shown in FIG. 30. The patient data entry screen contains patient information entry fields 202, which may include the patient's name, age, a unique identifier, contact information (e.g., address, telephone, etc.), gender, etc. Upon activation of one of the entry fields 202, such as by tapping, a virtual keyboard 204 may be presented to facilitate entry of information or data into the various fields, as shown in FIG. 31. The keyboard 204 may be hidden by pressing the keyboard icon 206. In certain instance, the patient information may already be stored on the system 10, so that entry of certain information within a portion of the fields 202 may populate the remaining fields.

The ordering screens may also be provided with various data entry category icons, such as the icons 208A-208D, which represent the categories of patient information 208A, prescription information 208B, frame information 208C, and previous lens information 208D. Other information categories may also be provided in addition to those listed.

The category icons 208A-208D may also be provided with an appearance alter feature that indicates the status of whether information for the different categories has been entered. This may constitute a status bar or portion 210 of the icon 208, such as the status bar 60, previously described. The status bar 210 is provided with an initial selected color or appearance to indicate a particular status. Upon completion of the data entry for each category corresponding to the particular icon 208, the appearance alter feature causes the icon 208 to change in appearance, such as a change in the color of the status bar 210. Thus, upon completion or entry of the patient data in the patient data fields 202 of screen 200, status bar 210A may be altered in appearance, e.g., green, to indicate that all information has been entered.

Figure 32:
FIG. 32 is a plan view of a prescription information screen of the display of the device of FIG. 4 shown with prescription information fields in accordance with an illustrative embodiment of the invention.

The user may then select to enter prescription information by activating prescription information icon 208B. Upon activation of prescription information icon 208B, a prescription information screen 212 is presented in the display 26 of the device 10, as shown in FIG. 32. The prescription information screen 212 is provided with prescription information fields 214 where various lens prescription information may be entered for the subject or patient. A virtual numerical keypad 218 may also be provided for information on the screen 212, as well as other ordering screens as described herein. The virtual keyboard 204 may also be automatically presented when fields requiring non-numerical data are activated. Upon completion of the prescription information fields 214, the status bar 210B may be automatically altered in appearance to indicate that all prescription information is complete.

In some embodiments, additional information screens may be provided with the system 10. This may include a frame information screen (not shown) that presents fields filled with the data already taken from the measurements for the subject, as previously described. Other screens may include a previous lens information screen (not shown) of the particular subject or patient. Such screen may be presented by activating icon 208D. This and other information screens may be provided with the system 10.

The user may return to any of the previous screens by touching or activating the various icons 208A-208D.

Once the ordering data is entered, the user may actuate an ordering transmission icon 216 wherein the measurements, patient and other data and information entered and provided to and by the system 10 is securely transmitted via the system's 10 communication unit 22 to a network through various communication links (wire, wireless, fiberoptics, etc.) to a manufacturer or processing facility to facilitate the manufacture of the final lenses for the subject based upon the transmitted information.

In certain embodiments, a product that provides the functions as they have been described may be provided as a computer program product that is loaded or provided on devices or systems, such as the device 10. This may be in the form of an application that is downloaded to the device from remote location through a communication link.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. A method of taking an ophthalmic measurement for the customization of eyeglasses with an electronic handheld device having a touchscreen display and a camera unit for producing digital photographic images with the handheld device that are displayed on the touchscreen display in real time, the handheld device having a orientation sensing unit for determining the orientation of the handheld device, the method comprising:

in an ophthalmic measurement selection mode of the device:
providing an ophthalmic measurement selection prompt on the touchscreen display that allows the alternate selection of at least two different ophthalmic measurements for the customization of eyeglasses;

in an image capturing mode of the device:
providing an ophthalmic measurement camera viewfinder screen on the touchscreen display corresponding to the selected ophthalmic measurement made from the ophthalmic measurement selection prompt;
positioning a subject wearing a spectacle frame on the subject's head at a position so that real time images of the subject's head with the spectacle frame from the camera unit are displayed in the ophthalmic measurement camera viewfinder screen of the touchscreen display while in the image capturing mode;
moving the electronic handheld device with the real time images of the at least a portion of the subject's head and spectacle frame being displayed within the display until the orientation sensing unit of the handheld device measures that the handheld device is at a selected oriented position; and
upon initiating an image capture instruction automatically capturing and storing on the electronic handheld device a single, non-transitory digital photographic image of the subject's head and spectacle frame for the selected ophthalmic measurement only at the moment the orientating sensing unit measures that the handheld device is at the selected oriented position; and in an ophthalmic measurement mode of the device:
   providing an ophthalmic measurement screen on the touchscreen display;
   making at least one ophthalmic measurement with the handheld device using the previously captured and stored single, non-transitory digital photographic image using an ophthalmic measurement device that is displayed on the touchscreen display that is manually manipulated to facilitate making the ophthalmic measurement, the ophthalmic measurement comprising at least one of a pantoscopic tilt measurement, a face form angle measurement, a vertex distance measurement, a seg height measurement, a spectacle frame dimension measurement, and a pupillary distance measurement.

2. The method of claim 1, wherein:
an orientation icon is displayed on the touchscreen display in the image capturing mode that indicates whether the handheld device is at or near the selected orientation.

3. The method of claim 1, wherein:
the at least one ophthalmic measurement is a pantoscopic tilt measurement.

4. The method of claim 1, wherein:
the at least one ophthalmic measurement is a face form angle measurement.

5. The method of claim 1, wherein:
the at least one ophthalmic measurement is vertex distance measurement.

6. The method of claim 1, wherein:
the at least one ophthalmic measurement is seg height measurement.

7. The method of claim 1, wherein:
the at least one ophthalmic measurement is spectacle frame dimension measurement.

8. The method of claim 1, wherein:
the at least one ophthalmic measurement is pupillary distance measurement.

9. The method of claim 1, wherein:
the handheld device has a length of from 6 to 12 inches and a width of from 4 to 10 inches.

10. The method of claim 1, wherein:
a transparent or translucent ghost image that is generated in the display in the image capturing mode that allows the real time images of the subject to be transmitted therethrough, the ghost image facilitating positioning real time images of the subject's head within the touchscreen display.

11. The method of claim 1, further comprising:
positioning a reference device having a known dimension adjacent to the spectacle frame in the image capturing mode so that the reference device appears in the real time images and the captured image.

12. The method of claim 1, wherein:
the electronic handheld device includes a camera selection control that allows the handheld device to be selectively switched to the image capturing mode.

13. The method of claim 1, further comprising:
associating subject or patient data with the ophthalmic measurement made on the electronic handheld device and transmitting said associated subject or patient data and the ophthalmic measurement from the electronic handheld device through a network to a manufacturing or processing facility to facilitate manufacturing of a lens from the transmitted measurement.

14. A mobile handheld ophthalmic measuring system for the customization of eyeglasses comprising:
   a housing;
   a computer processing system;
   a touchscreen display;
   a camera unit for producing digital photographic images with the handheld device that are displayed on the touchscreen display in real time;
   an orientation sensing unit for determining the orientation of the handheld device;
   a camera control that allows the camera unit to be selectively switched to an image capturing mode wherein an ophthalmic measurement camera viewfinder screen is displayed on the touchscreen display, and wherein the camera unit automatically captures a single, non-transitory image for a particular ophthalmic measurement for the customization of eyeglasses upon receiving an image capture instruction only at the moment the orientation sensing unit measures the handheld device is at a selected orientation in the image capturing mode;
   an ophthalmic measurement prompt that is displayed on the touchscreen display that corresponds to each of a pantoscopic tilt measurement, a face form angle measurement, a vertex distance measurement, a seg height measurement, a spectacle frame dimension measurement, and a pupillary distance measurement;
   a transparent or translucent ghost image that is generated in the display that allows the real time images of the subject to be transmitted therethrough, the ghost image facilitating positioning of real time images within the touchscreen display; and
   at least one ophthalmic measuring device that is usable with the captured image to make at least one ophthalmic measurement that is displayed on the touchscreen display that is manually manipulated to facilitate making the at least one ophthalmic measurement.

15. The measuring system of claim 14, wherein:
an orientation icon is displayed on the touchscreen display that indicates whether the handheld device is at or near the selected orientation.

16. The measuring system of claim 14, wherein:
the housing has a length of from 6 to 12 inches and a width of from 4 to 10 inches.

17. The measuring system of claim 14, further comprising:
an image recognition unit that is capable of recognizing a reference device within a photographic image having a known dimension to facilitate measurement of a dimension of another object within said photographic image.

18. The measurement system of claim 14, wherein:
the at least one ophthalmic measuring device is an angle measurement device.

19. The measurement system of claim 14, wherein:
the at least one ophthalmic measuring device is a spatial dimension measurement device.

20. The system of claim 14, further comprising:
an ordering prompt that is displayed on the touchscreen display to facilitate ordering of ophthalmic lenses measured with the mobile handheld ophthalmic measuring system.

* * * * *